US012805769B2

(12) United States Patent
Choy et al.

(10) Patent No.: US 12,805,769 B2
(45) Date of Patent: Nov. 24, 2026

(54) SENSOR IDENTIFICATION AND INTEGRITY CHECK DESIGN

(71) Applicant: MEDTRONIC MINIMED, INC., Northridge, CA (US)

(72) Inventors: David Yueh-hua Choy, San Gabriel, CA (US); Ellis Garai, Woodland Hills, CA (US); Melissa Tsang, Encino, CA (US); Anuj M. Patel, Porter Ranch, CA (US)

(73) Assignee: Medtronic MiniMed, Inc., Northridge (CA)

( * ) Notice: Subject to any disclaimer, the term of this patent is extended or adjusted under 35 U.S.C. 154(b) by 198 days.

(21) Appl. No.: 18/780,007

(22) Filed: Jul. 22, 2024

(65) Prior Publication Data

US 2024/0374174 A1 Nov. 14, 2024

Related U.S. Application Data

(63) Continuation of application No. 16/944,450, filed on Jul. 31, 2020, now Pat. No. 12,082,924.

(51) Int. Cl.

| | |
|---|---|
| ***A61B 5/145*** | (2006.01) |
| ***A61B 5/00*** | (2006.01) |
| ***A61B 5/1495*** | (2006.01) |

(52) U.S. Cl.

CPC ........ *A61B 5/14532* (2013.01); *A61B 5/1495* (2013.01); *A61B 5/4839* (2013.01);

(Continued)

(58) Field of Classification Search

CPC . A61B 5/14532; A61B 5/1473; A61B 5/1486; A61B 5/1495; A61B 5/4839;

(Continued)

(56) References Cited

U.S. PATENT DOCUMENTS

| | | | |
|---|---|---|---|
| 4,028,621 A | 6/1977 | Bloxam | |
| 4,755,173 A | 7/1988 | Konopka et al. | |

(Continued)

FOREIGN PATENT DOCUMENTS

| | | |
|---|---|---|
| CN | 108362867 A | 8/2018 |
| CN | 109310372 A | 2/2019 |

(Continued)

OTHER PUBLICATIONS

CN Office Action dated Mar. 20, 2025 in CN Application No. 202180058316.4, with English Translation.

(Continued)

*Primary Examiner* — Jennifer Robertson
*Assistant Examiner* — Nidhi N Patel
(74) *Attorney, Agent, or Firm* — Weaver Austin Villeneuve & Sampson LLP

(57) ABSTRACT

An analyte sensor device includes a housing, a sensor, and a printed circuit board assembly (PCBA) within the housing and including a circuit and a first plurality of contacts. The sensor includes a proximal end within the housing and a distal end outside of the housing. The proximal end includes a second plurality of contacts electrically connected to the first plurality of contacts on the PCBA. The distal end includes one or more electrodes configured to measure a concentration level of an analyte in a body of a user. The circuit is operable to detect electrical connection between the first plurality of contacts and the second plurality of contacts within the housing while the distal end of the sensor is outside the body of the user or a fluid.

20 Claims, 31 Drawing Sheets

(52) U.S. Cl.
CPC ................. *A61B 2560/0214* (2013.01); *A61B 2560/0223* (2013.01); *A61B 2562/166* (2013.01); *A61B 2562/227* (2013.01)

(58) Field of Classification Search
CPC .... A61B 2560/0214; A61B 2560/0223; A61B 2560/0276; A61B 2562/166; A61B 2562/226; A61B 2562/227
See application file for complete search history.

(56) References Cited

U.S. PATENT DOCUMENTS

| | | | |
|---|---|---|---|
| 5,391,250 | A | 2/1995 | Cheney, II et al. |
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Vanantwerp et al. |
| 6,017,328 | A | 1/2000 | Fischell et al. |
| 6,175,752 | B1 | 1/2001 | Say et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,418,332 | B1 | 7/2002 | Mastrototaro et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van et al. |
| 8,353,829 | B2 | 1/2013 | Say et al. |
| 12,082,924 | B2 | 9/2024 | Choy et al. |
| 2007/0123819 | A1 | 5/2007 | Mernoe et al. |
| 2008/0133146 | A1 | 6/2008 | Chang et al. |
| 2010/0160861 | A1 | 6/2010 | Causey, III et al. |
| 2017/0127982 | A1 | 5/2017 | Larson et al. |
| 2017/0181676 | A1 | 6/2017 | Nogueira et al. |
| 2017/0290534 | A1 | 10/2017 | Antonio et al. |
| 2019/0117133 | A1 | 4/2019 | Halac et al. |
| 2020/0025707 | A1 | 1/2020 | Beaty |
| 2020/0268295 | A1 | 8/2020 | Hwang et al. |
| 2021/0209497 | A1 | 7/2021 | Wang et al. |
| 2022/0031205 | A1 | 2/2022 | Choy et al. |

FOREIGN PATENT DOCUMENTS

| | | | |
|---|---|---|---|
| CN | 111094961 | A | 5/2020 |
| CN | 116075270 | A | 5/2023 |
| WO | 2022026542 | A1 | 2/2022 |

OTHER PUBLICATIONS

EP Office Action dated Jan. 25, 2024 in EP Application No. 21756141.4.
International Preliminary Report on Patentability and Written Opinion dated Feb. 9, 2024 in PCT Application No. PCT/US2021/043443.
International Search Report and Written Opinion dated Oct. 21, 2021 in PCT Application No. PCT/US2021/043443.
U.S. Advisory Action dated Apr. 18, 2023 in U.S. Appl. No. 16/944,450.
U.S. Final Office Action dated Jan. 31, 2023 in U.S. Appl. No. 16/944,450.
U.S. Non-Final Office Action dated Dec. 8, 2023 in U.S. Appl. No. 16/944,450.
U.S. Non-Final Office Action dated Jun. 21, 2022 in U.S. Appl. No. 16/944,450.
U.S. Notice of Allowance dated Apr. 24, 2024 in U.S. Appl. No. 16/944,450.
U.S. Restriction Requirement dated Mar. 7, 2022 in U.S. Appl. No. 16/944,450.
EP Office Action dated Sep. 12, 2025 in EP Application No. 21756141.4.
AU Office Action dated Mar. 16, 2026 in AU Application No. 2021318974 [A0002993AU01].
CA Office Action dated Sep. 14, 2026 in CA Application No. 3190321.

| Pin | During Test Pin State | After Test |
|---|---|---|
| X | Digital Output set to 1 | Digital (high-impendence) Input |
| Y | Digital Input | Digital (high-impendence) Input |

Contact Pad Diameter: 22 mils
Contact Pad Pitch: 50 mils

| Pin | During Test Pin State | After Test |
|---|---|---|
| X | Digital Output set to 1 | Digital (high-impendence) Input |
| Y | Analog Input | Digital (high-impendence) Input |

| Pin | During Test Pin State | After Test |
|---|---|---|
| X | Digital Output set to 1 | Digital (high-impendence) Input |
| Y | Analog Input | Digital (high-impendence) Input |

SENSOR IDENTIFICATION AND INTEGRITY CHECK DESIGN

CROSS-REFERENCE TO RELATED APPLICATION

This application is a continuation of U.S. Non-Provisional patent application Ser. No. 16/944,450, filed Jul. 31, 2020, titled "SENSOR IDENTIFICATION AND INTEGRITY CHECK DESIGN," which is hereby incorporated by reference in its entirety for all purposes.

TECHNICAL FIELD

This application relates generally to analyte sensors.

BACKGROUND

Electrochemical sensors are commonly used to detect or measure the concentrations of in vivo analytes, such as glucose. Typically in such analyte sensing systems, an analyte (or a species derived from it) is electro-active and generates a detectable signal at an electrode in the sensor. This signal is then correlated with the presence or concentration of the analyte within a biological sample. In some conventional sensors, an enzyme is provided that reacts with the analyte to be measured, the byproduct of the reaction being qualified or quantified at the electrode. In one conventional glucose sensor, immobilized glucose oxidase catalyzes the oxidation of glucose to form hydrogen peroxide, which is then quantified by amperometric measurements (e.g., change in electrical current) through one or more electrodes.

It is desirable that glucose sensors be reliable and that faulty devices or faulty electrical connections are identified prior to use. Currently there is no automated test ensuring the electrode sensor is making proper electrical connection to the electronics controlling the electrodes. One or more embodiments described herein satisfy this need.

SUMMARY

The present disclosure describes a testing system for an analyte sensing apparatus comprising a sensing portion (making contact with an analyte) and electronics connected to the sensing portion (for processing the signals outputted from the sensing portion). More specifically, the analyte sensing apparatus comprises (e.g., unique) electrical connections or features on the sensor portion and in the electronics (e.g., on a printed circuit board) that enable testing of the sensor portion connection to the electronics without contacting the analyte.

According to certain embodiments, an analyte sensor device includes a housing, a sensor, and a printed circuit board assembly (PCBA) within the housing and including a circuit and a first plurality of contacts. The sensor includes a proximal end within the housing and a distal end outside of the housing. The proximal end includes a second plurality of contacts electrically connected to the first plurality of contacts on the PCBA. The distal end includes one or more electrodes configured to measure a concentration level of an analyte in a body of a user. The circuit is operable to detect electrical connection between the first plurality of contacts and the second plurality of contacts within the housing while the distal end of the sensor is outside the body of the user or a fluid.

In one or more examples, the electrical features are designed to be powered on only during Device Level Testing (DLT) and are then powered off so as to not interfere with the sensor operation during normal use. Some embodiments include a resistor of a certain value fabricated directly on the sensor portion in order to both detect the sensor portion is present (electrically connected) and also to identify the type of sensing portion (e.g., a first type or product line of sensor portion versus a second type or product line of sensor portion). In one or more examples, the electrical features eliminate the potential of delivery of a faulty device to a user.

In one or more further examples, the electronics includes a Device Level Tester (DLT) unit that only integrates the testing if there is a leak between contacts pads. If there is no sensor portion assembled, the DLT will pass the current leak test it performs to a control processor in the analyte sensor apparatus.

In one embodiment, the analyte sensor apparatus comprises a sensing portion including one or more electrodes including a working electrode; an analyte sensing layer on the working electrode, wherein the analyte sensing layer detectably alters an electrical current at the working electrode in a presence of an analyte; and a plurality of contacts for electrically connecting the one or more electrodes to a printed circuit board assembly (PCBA). The analyte sensor apparatus further includes a circuit comprising one or more of the contacts, the circuit detecting an electrical connection between the one or more of the contacts and the PCBA without requiring exposure of the sensor portion to a fluid. The PCBA comprises one or more processors for receiving the electrical current and determining a concentration level of the analyte from the electrical current. In one or more examples, the sensor portion comprises a flexible sensor portion. In yet further examples, the sensor portion comprises a sensor flex.

The circuit, the PCBA, and the one or more contacts can be configured in a variety of ways. In one embodiment, the contacts include a first contact (T) and the PCBA further includes a plurality of sensor connection contacts for electrically connecting the PCBA to the sensing portion. The sensor connection contacts include a second contact (A) and a third contact (B) and the sensor portion in operable connection with the PCBA causes the first contact to physically contact both the second contact (A) and the third contact (B) so as to form the electrical connection between the second contact (A) and the second contact (B). The circuit detects the electrical connection comprising a conduction path between the second contact and the third contact formed by the first contact physically contacting both the second contact (A) and the third contact (B).

In another embodiment, the contacts include a first contact (T) and the sensor connection contacts on the PCBA include a second contact (A), a third contact (B), and a fourth contact (C). The PCBA further includes a first conductive track electrically connecting the second contact (A) to the fourth contact (C). The analyte sensor apparatus further includes an elastomer connector comprising a second conductive track so that the sensor portion in operable connection with the PCBA comprises the elastomer connector pressing the first contact (T) into physical contact and electrical contact with the fourth contact (C) and the second conductive track electrically connects the second contact (A) to the third contact (B). In this way, the first conductive track and the second conductive track form the electrical connection between the fourth contact (C), the third contact (B), the second contact (A), and the first contact (T). The circuit detects the electrical connection comprising a conduction path between the second contact (A) and the third contact (B).

In yet another embodiment, the analyte sensor apparatus further comprises an elastomer connector including a conductive track and the PCBA comprises a plurality of sensor connection contacts including a second contact (A) and a third contact (B). The contacts on the sensor portion comprise a first contact for electrically connecting one of the electrodes (e.g., a counter electrode) to the PCBA. The first contact is on a back side of the sensor portion facing away from the PCBA. The sensor portion in operable connection with the PCBA comprises the conductive track forming the electrical connection between the first contact, the second contact (A), and the third contact (B).

In yet a further embodiment, the analyte sensor apparatus further comprises an elastomeric connector including a plurality of conductive tracks and the PCBA comprises a plurality of sensor connection contacts including a second contact (A) and a third contact (B). The contacts on the sensor portion electrically connect the electrodes to the PCBA. The sensor portion in operable connection with the PCBA comprises each of the conductive tracks electrically connecting one of the contacts to one of the plurality of sensor connection contacts, and one of the conductive tracks forming the electrical connection between a first contact on the sensor portion, the second contact (A), and the third contact (B).

In another embodiment, the PCBA comprises a plurality of sensor connection contacts including a second contact (A) and a third contact (B) and processor. The processor comprises an output for applying a voltage V to one of the electrodes and the output is electrically connected to the second contact (A). The processors further includes a check input electrically connected to the third contact (B) so as to detect the electrical connection between the second contact (A), the third contact (B) and one or more of the contacts on the sensor portion.

In one or more examples, the electrical connection comprises a conduction path characterized by a potential difference between the second contact (A) and the third contact (B) being less than 10% of a voltage applied by the circuit to the second contact (A) or the third contact (B), the voltage being applied to measure the electrical connection.

In yet another embodiment, the contacts on the sensor portion comprise a first test contact and a second test contact; and the sensing portion includes a first resistor electrically connecting the first test contact to the second test contact. The circuit further includes a second resistor on the PCBA and connected in series with the first resistor and the circuit measures a test voltage at a node between the first resistor and the second resistor so as to measure a potential difference across the first resistor. The potential difference is used to detect, measure, or characterize the electrical connection. In various examples, the test voltage measured above a predetermined threshold confirms that the electrical connection is sufficient for measuring the concentration of the analyte using the working electrode.

In one or more embodiments the first resistor has a resistance tagging the sensor portion so that the test voltage can be used to identify at least one of (a) a product line associated with sensor portion, (2) a type of analyte measured using the sensor portion, (3) a batch or lot comprising the sensor portion, or (4) a calibration needed to measure the concentration level using the sensor portion. In yet further examples, the analyte sensor apparatus further includes a transmitter transmitting the first resistance and/or test voltage, off the analyte sensor apparatus, to a computer system tracking the sensor portion and/or providing updates using information determined from the first resistance.

In yet a further embodiment, the analyte sensor apparatus includes or is operatively connected to a computer implemented system comprising the one or more processors; one or more memories; and one or more programs or algorithms stored in the one or more memories. The one or more programs or algorithms executed by the one or more processors determine the first resistance from the test voltage and use the first resistance to determine the type of analyte. In another embodiment, the one or more programs or algorithms executed by the one or more processors determine the first resistance from the test voltage and use the first resistance to calculate the concentration level of the analyte.

In yet another embodiment, the circuit comprises a switch (1) activating the circuit during a device level testing mode of the analyte sensor apparatus and (2) powering off the circuit after the electrical connection is detected, so that the circuit is de-activated during normal operation of the analyte sensor apparatus measuring the concentration level of the analyte using the electrical current.

In yet a further embodiment, the analyte sensor apparatus includes a battery connected to the processors for powering the processors; an elastomer; and a housing housing the PCBA, the battery, and the elastomer. The housing comprises a top portion and a bottom portion, wherein closure of the housing attaching the top portion to the bottom portion clamps the contacts between the elastomer and the PCBA so as to cause physical contact and the electrical connection between the contacts and the sensor connection contacts on the PCBA. The analyte sensor apparatus further includes an insertion needle connected to the sensing portion. The circuit outputs a test signal in response to detecting the electrical connection, and the one or more of the processors compute the concentration level of the analyte using the electrical current after (1) receiving the test signal indicating the proper electrical connection of the PCBA to the sensing portion; and (2) deployment of the sensing portion by the insertion needle into the environment inside a body when the housing is attached to an exterior of the body. In one example, the analyte sensor apparatus comprises a glucose sensor and the analyte sensing layer includes an enzyme having a composition that reacts with the analyte, comprising glucose, to form a byproduct, and the byproduct detectably alters the electrical current at the working electrode. The test signal indicates the electrical connection enabling the processors to compute the concentration level of glucose useful for determining an administration of insulin to the body of a diabetic patient. In various examples, a system comprising an insulin pump is connected to the analyte sensor apparatus and the insulin pump delivers insulin to the diabetic patient depending on the concentration level measured after the one or more processors receive the test signal indicating the adequate electrical connection.

The present disclosure further describes a method of testing an analyte sensor apparatus, comprising providing a sensing portion including one or more electrodes including a working electrode; an analyte sensing layer on the working electrode (wherein the analyte sensing layer detectably alters an electrical current at the working electrode in a presence of an analyte); and a plurality of contacts for electrically connecting the one or more electrodes to a printed circuit board assembly (PCBA). The method further comprises detecting an electrical connection using a circuit comprising one or more of the contacts. The circuit detects the electrical connection between the one or more of the contacts and the PCBA without requiring exposure of the sensing portion to a fluid (e.g., solution comprising water). The PCBA comprises one or more processors for receiving the electrical current and determining a concentration level of the analyte from the electrical current. In various examples, the circuit outputs a test signal in response to detecting the electrical connection and the test signal is used to identify the sensor portion. In yet further examples, the circuit detects the electrical connection in a non-hydrated environment.

In yet another embodiment, the method further comprises powering off the circuit after detecting the electrical connection so that the circuit is de-activated during normal operation of the analyte sensor apparatus measuring a concentration level of the analyte using the electrical current.

The present disclosure further describes a method of making an analyte sensor apparatus, comprising providing a sensing portion including one or more electrodes including a working electrode; an analyte sensing layer on the working electrode (wherein the analyte sensing layer detectably alters an electrical current at the working electrode in a presence of an analyte); and a plurality of contacts for electrically connecting the one or more electrodes to a printed circuit board assembly (PCBA). The method further comprises providing a circuit comprising one or more of the contacts. The circuit detects an electrical connection between the one or more contacts and the PCBA without requiring exposure of the sensing portion to a fluid. The PCBA comprises one or more processors for receiving the electrical current and determining a concentration level of the analyte from the electrical current.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

As shown in FIG. 3, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (Isig) that is output from the potentiostat.

DETAILED DESCRIPTION OF THE INVENTION

Figure 1A:
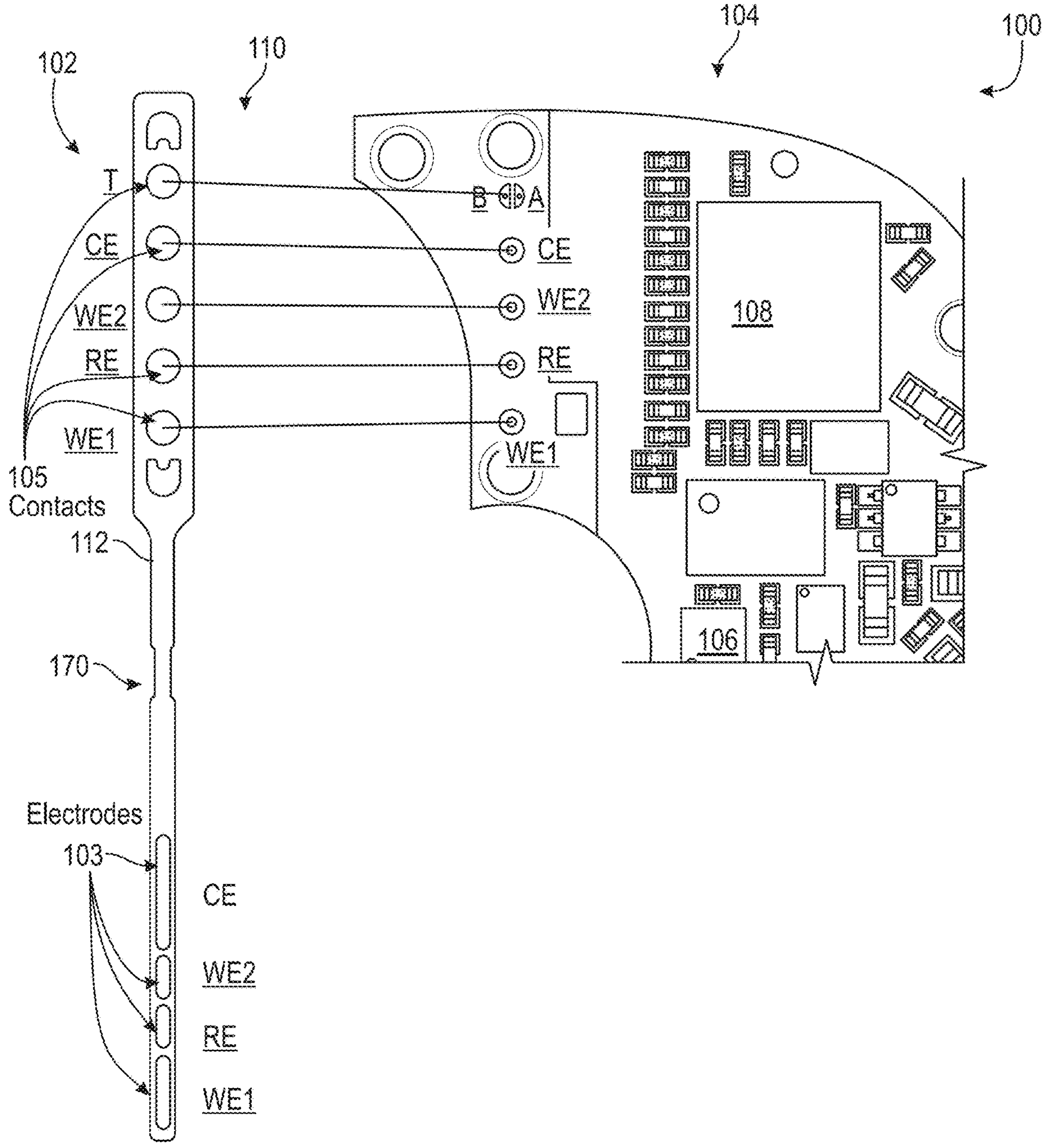
FIG. 1A illustrates electrical connection between a sensor portion and a printed circuit board assembly (PCBA), according to one or more examples. Conductive surfaces or pads CE, WE2, RE, WE1 shown in yellow are connected to electrodes (depicted in gray) CE, WE2, RE, WE1, respectively.

Unless otherwise defined, all terms of art, notations, and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All numbers recited in the specification and associated claims that refer to values that can be numerically characterized with a value other than a whole number (e.g., a thickness) are understood to be modified by the term "about." Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Furthermore, all publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors elements, including for example, those disclosed in U.S. patents application Nos. 20050115832, 20050008671, 20070227907, 20400025238, 20110319734, 20110152654 and Ser. No. 13/707,400 filed Dec. 6, 2012, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042, 625, and WO 03/074107, and European Patent Application EP 1153571, the contents of each of which are incorporated herein by reference.

A. Illustrative Embodiments of the Invention and Associated Characteristics

Example Apparatus

FIGS. 1A-1D illustrate various components of an analyte sensor apparatus 100. FIG. 1A illustrates the analyte sensor apparatus 100 comprises a sensing portion 102 including one or more electrodes 103 comprising working electrodes (WE1, WE2); a counter electrode (CE), and a reference electrode (RE). In various examples, the sensor portion is flexible or comprises a sensor flex.

FIG. 1A further illustrates the sensor portion 102 includes a plurality of contacts 105 (e.g., conductive surfaces, metal layers or regions, metallization, or contact pads comprising metal) electrically connected to the one or more electrodes via conductive tracks through the sensor portion 102. In this way, the contacts 105 (CE, WE1, WE2, RE) comprise the electrical connections 110 between the sensor portion 102 and a printed circuit board assembly (PCBA), electrically connecting the one or more electrodes 103 (CE, WE1, WE2, RE) to the PCBA.

FIG. 1A further illustrates the analyte sensor apparatus comprises one or more circuits 104 comprising one or more processors 106, 108 for controlling the functioning of the electrodes as illustrated herein and measuring proper operable electrical connection between the sensor portion (including electrodes) and the PCBA.

The sensing 102 portion further comprises an electrical insulator 112. The working electrode, the test electrodes, the counter electrode, and the reference electrode are disposed on a surface of the electrical insulator at a distal end of the sensor portion. The distal end is inserted into the in-vivo or in-vitro environment (e.g., interstitial tissue or space) during measurement of the analyte using the working electrode. The contacts are disposed on a proximal end of the sensor portion that is not inserted into the in-vivo or in-vitro environment.

Figure 1B:
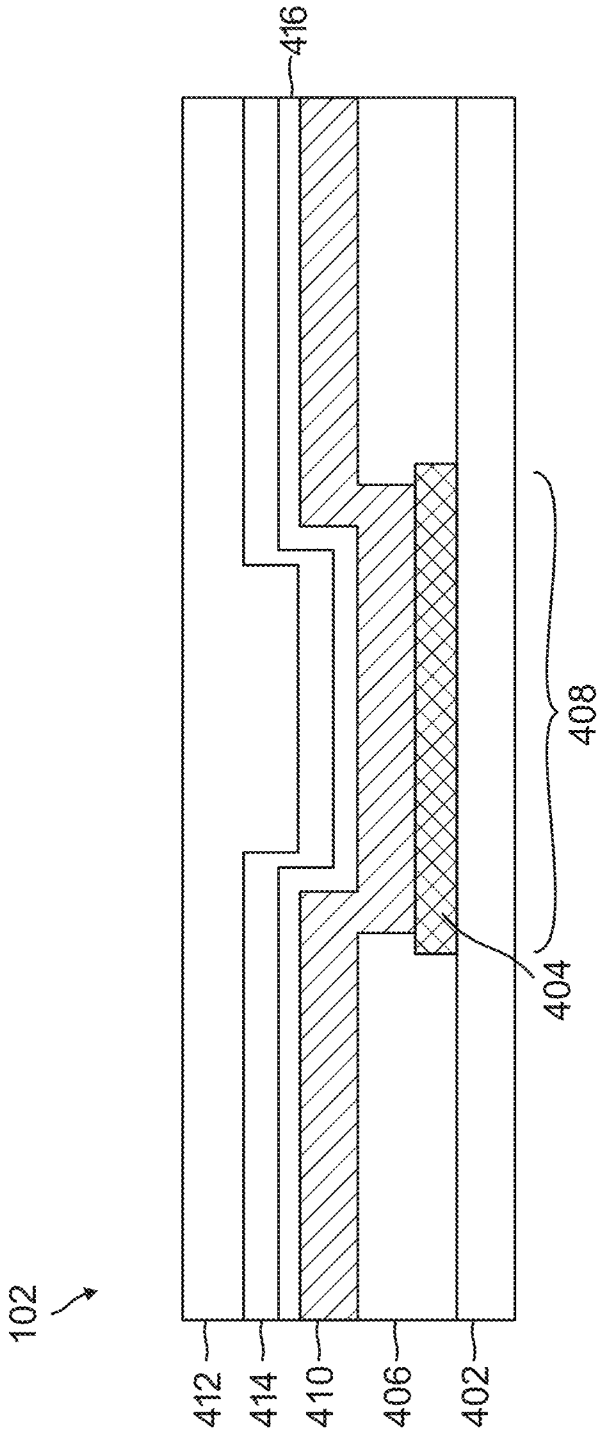
FIG. 1B shows an illustration of amperometric analyte sensors formed from a plurality of planar layered elements.

FIG. 1B further illustrates the sensing portion 102 further includes an analyte sensing layer 410 on the working electrode 404 wherein the analyte sensing layer detectably alters an electrical current at the working electrode in a presence of an analyte. The sensing portion further comprises an analyte modulation layer 412, a protein constituent 416, an adhesion promoting constituent 414, a cover 406, and a base constituent 402.

Figure 1C:
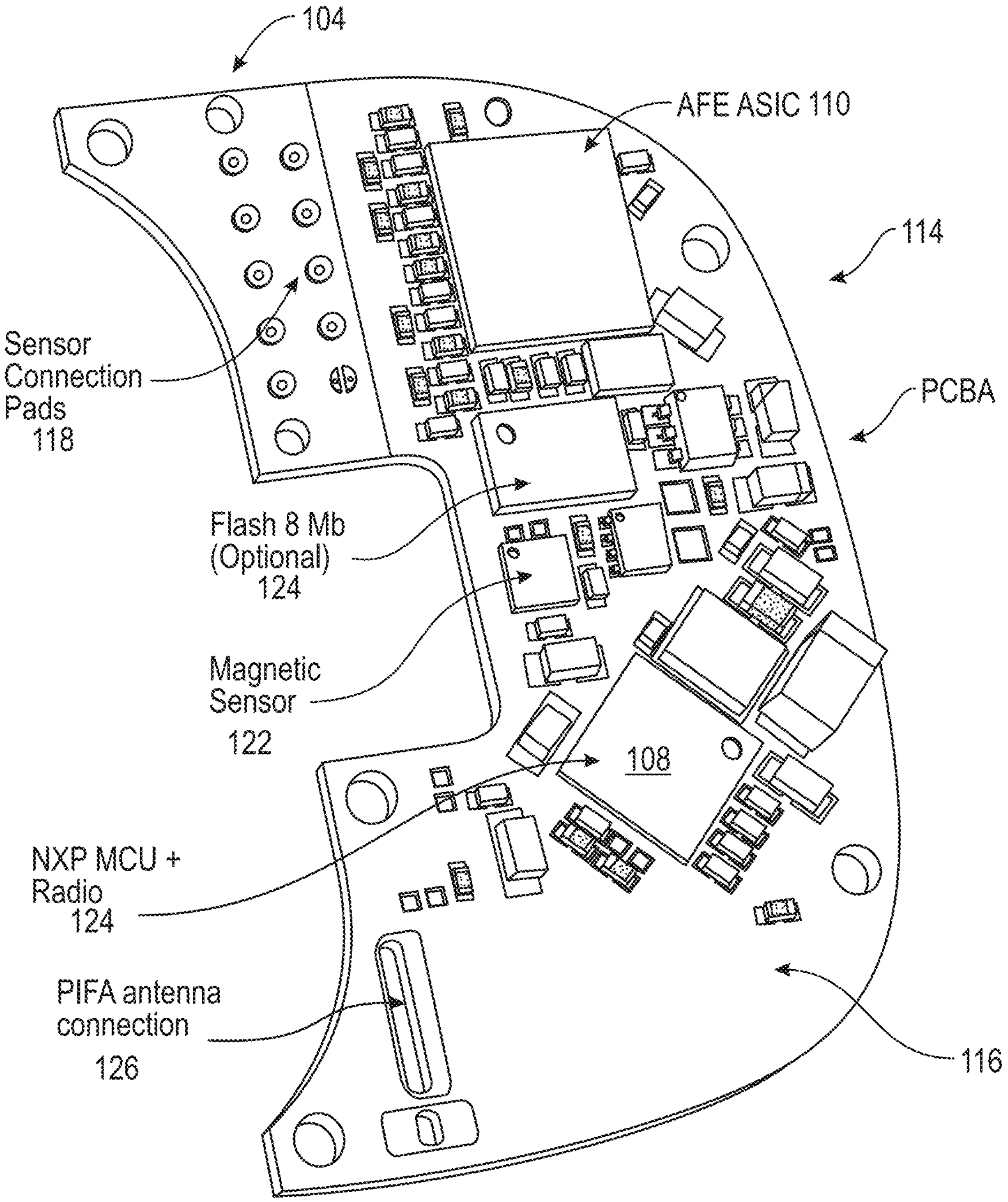
FIG. 1C illustrates a PCBA comprising a transmitter, according to one or more examples.

FIG. 1C illustrates electronic circuitry 114 comprising the one or more circuits 104 and other circuits for controlling the functioning of the analyte sensor apparatus 100. FIG. 1C illustrates the PCBA comprises at least a portion of the electronic circuitry 114 disposed on and electrically connected using a printed circuit board (PCB) including a plurality of conductive tracks 116. The electronic circuitry 114 further comprises sensor connection contacts 118 (e.g., contact pads), a processor 108, optional memory 120 (e.g., flash memory, e.g., 8 Megabytes), magnetic sensor 122, a transmitter 124 (including radio), and an antenna 126 (e.g., planar inverted F antenna, PIFA). Example processors 108 and transmitters 124 include, but are not limited to, an application specific integrated circuit (ASIC), e.g., analog front end (AFE) ASIC, and a microcontroller unit (MCU), e.g., NXP MCU.

In one or more aspects, the circuits 104 include an analyte sensing meter (e.g., glucose meter) including processors connected to the working electrode, counter electrode, and reference electrode via the sensor connection contacts 118 and contacts 105 and configured to compute the concentration level using the electrical current received from the working electrode.

In one or more aspects, the circuits 104 include a device level testing unit including a circuit 128 comprising one or more of the contacts 105, wherein the circuit 128 detects or measures the electrical connection 110 between one or more of the contacts 105 and the electronic circuitry 114 e.g., Printed Circuit Board Assembly (PCBA), independent of contact or exposure of the sensing portion to a fluid (e.g. even when the sensor portion is disconnected from the environment comprising the analyte). In one or more examples, the device level testing unit detects the electrical connection when the sensing portion is in a non-hydrating environment.

Figure 1D:
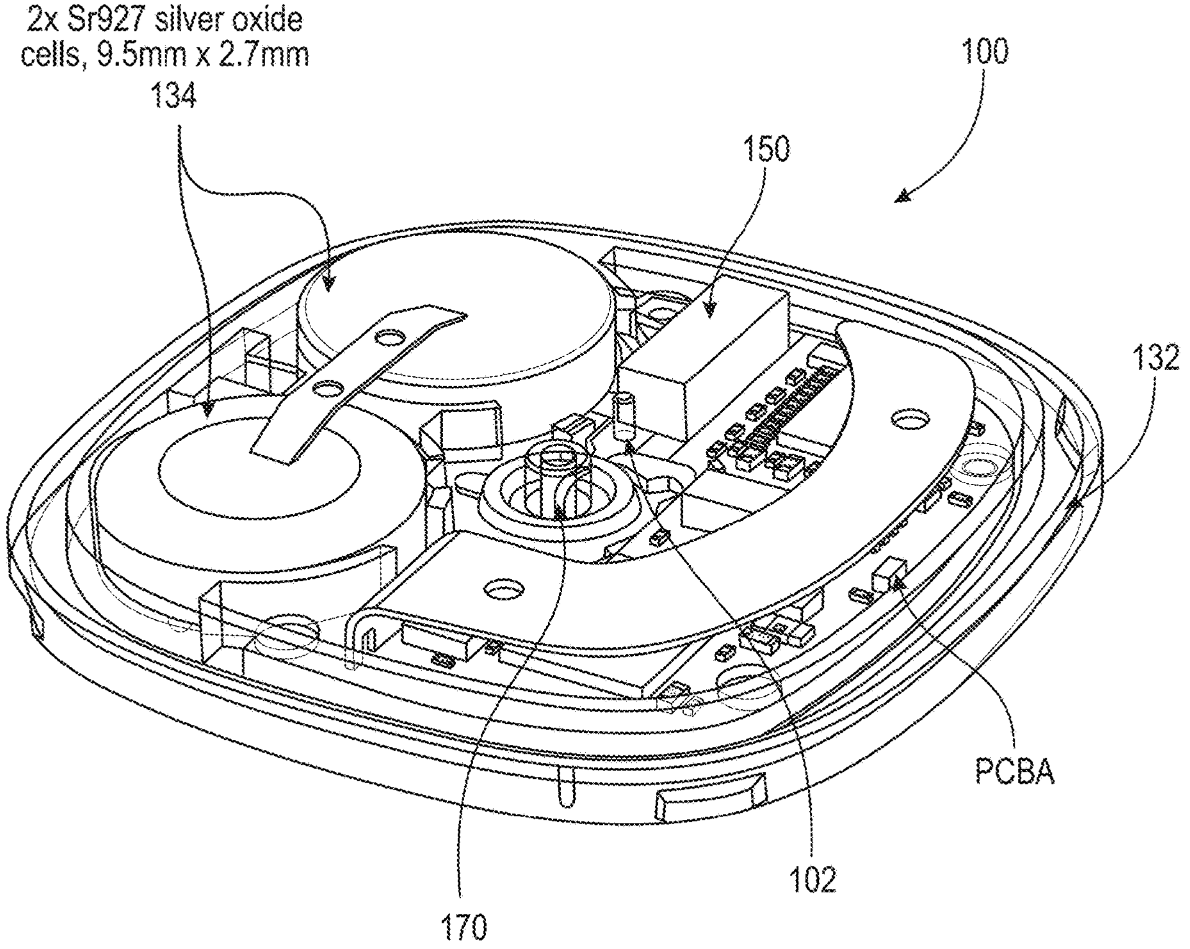
FIG. 1D illustrates a housing housing the PCBA and batteries for powering the PCBA.

FIG. 1D illustrates the analyte sensor apparatus 100 further comprises a housing 132 for housing the printed circuit board (PCBA), a battery 134 powering the PCBA and the sensing portion, and an elastomer 150 for clamping the proximal end 152 of the sensor portion 102 to the PCBA. The sensor portion includes a section extending through an opening in the housing so that the distal end of the sensor portion 102 is deployed by an insertion needle 170 into the in-vivo or in-vitro environment during measurement of the concentration level of the analyte.

Figure 1E:
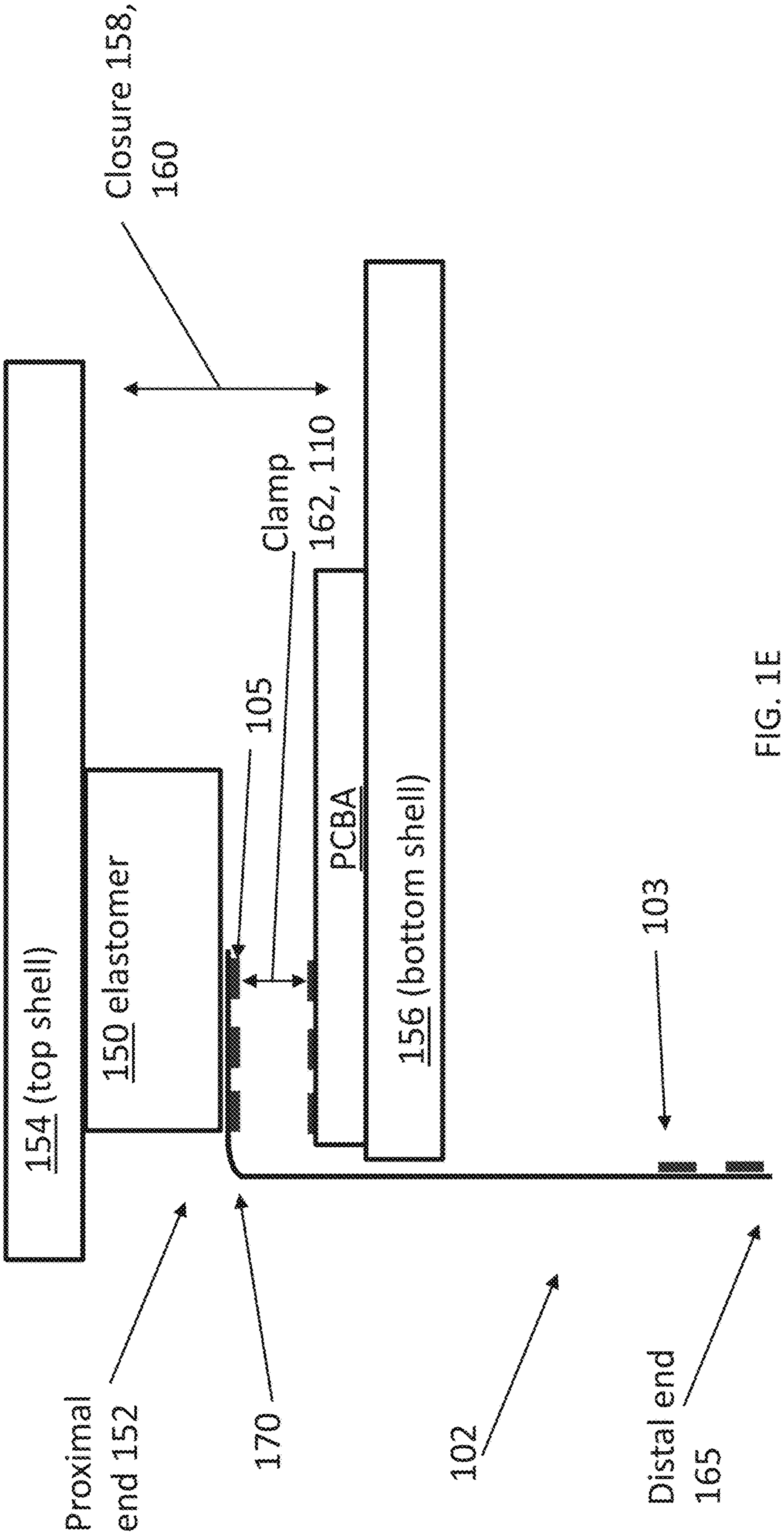
FIG. 1E is a side-view schematic illustrating electrical connection of the sensor portion to the PCBA.

FIGS. 1D and 1E illustrates the elastomer 150; the housing comprising a top portion 154 (top shell) and a bottom portion 156 (bottom shell), wherein closure 158 of the housing (attachment 160 of the top portion to the bottom portion) clamps 162 the contacts 105 between the elastomer and the PCBA so as to cause physical contact and the electrical connection 110 between the contacts 105 and sensor connection contacts 118 on the PCBA. Contacts 105 typically comprise a metal layer or metal region on the proximal end 152 the sensor portion. Electrodes 103 are located at the distal end 165 of the sensor portion 102 and are inserted into the in-vivo or in-vitro environment during operation of the analyte sensor apparatus. Sensor portion is bent at the neck or at a narrow portion 171 of the sensor portion during installation.

In one or more examples, the elastomer comprises an elastomeric connector 150 (e.g., ZEBRA connector) comprising of alternating conductive and insulating regions or tracks in a rubber or elastomer matrix.

Example Sensor Portion Configurations

The methods for forming analyte sensors that comprise the electrodes disclosed herein can include a number of steps. For example, such methods can include forming a working electrode, a counter electrode and a reference electrode on the base substrate and/or forming a plurality of contact pads on the base substrate, and/or forming a plurality of electrical conduits on the base substrate. In certain embodiments of the invention, the methods comprise forming a plurality of working electrodes, counter electrodes and reference electrodes clustered together in units consisting essentially of one working electrode, one counter electrode and one reference electrode. The electrodes are formed on the base substrate and these clustered units are longitudinally distributed on at least one longitudinal arm of the base substrate in a repeating pattern of units. Optionally in such methods, the working electrode is formed as an array of electrically conductive members disposed on the base substrate, the electrically conductive members are circular and have a diameter between 10 μm and 400 μm, and the array comprises at least 10 electrically conductive members. The methods can further comprise forming an analyte sensing layer on the working electrode, wherein the analyte sensing layer detectably alters the electrical current at the working electrode in the presence of an analyte. Typically these methods also include forming an analyte modulating layer on the analyte sensing layer, wherein the analyte modulating layer modulates the diffusion of analyte therethrough.

Yet another embodiment of the invention is an analyte sensor apparatus that includes a base substrate comprising a well that holds a metal electrode composition formed using a sputtering process. In such embodiments, the structure of the platinum composition is formed to include a central planar region and an edge or ridge like region that surrounds the central planar region. In such embodiments, the thickness or height of the metal composition at the edge is less than 2× the average thickness of metal composition in the central planar region. In certain embodiments of the invention, the well comprises a lip that surrounds the well; and the edge region of the metal composition is below the lip of the well. Typically in these embodiments, both the central planar region forms an electroactive surface of a working electrode in the sensor. Sensor embodiments of the invention typically include additional layers of material coated over the working electrode, for example an analyte sensing layer disposed over the working electrode, one that detectably alters the electrical current at the working electrode in the presence of an analyte as well as an analyte modulating layer disposed over the analyte sensing layer that modulates the diffusion of analyte therethrough.

In typical embodiments of the invention, the electrode is formed in a well of a base substrate comprising a dielectric material (e.g., a polyimide). Typically, the well includes a conductive material disposed at the bottom of the well (e.g., Au). Optionally the well in the base substrate is rectangular or circular. In certain embodiments of the invention, the base substrate comprises at least 10, 20 or 30 wells formed into a microarray. In typical sensor embodiments, a base substrate is formed so that it includes a well that comprises a lip surrounding the well. In certain processes disclosed herein, the metal composition is sputtered so that the metal composition is below the lip of the well. In addition, a variety of different electrically conductive elements can be disposed on the base substrate. In some embodiments of the invention, the base substrate comprises a plurality of reference electrodes, a plurality of working electrodes and a plurality of counter electrodes clustered together in units consisting essentially of one working electrode, one counter electrode and one reference electrode, and the clustered units are longitudinally distributed on the base substrate in a repeating pattern of units.

In one or more further examples, the electrodes comprise arrays of pillars (e.g., sputtered pillars).

Embodiments of the invention include further elements designed for use with the sensor apparatuses that are disclosed herein, for example those that are designed to analyze electrical signal data obtained from sputtered electrodes disposed on the base substrate. In some embodiments of the invention, the analyte sensor apparatus includes a processor and a computer-readable program code having instructions, which when executed, cause the processor to assess electrochemical signal data obtained from at least one working electrode and then compute analyte concentrations based upon the electrochemical signal data obtained from the working electrode. In certain embodiments of the invention, the processor compares electrochemical signal data obtained from multiple working electrodes in order to, for example, adapt different electrodes to sense different analytes, and/or to focus on different concentration ranges of a single analyte; and/or to identify or characterize spurious sensor signals (e.g. sensor noise, signals caused by interfering compounds and the like) so as to enhance the accuracy of the sensor readings.

In some embodiments of the invention, the base structure comprises a flexible yet rigid and flat structure suitable for use in photolithographic mask and etch processes. In this regard, the base structure typically includes at least one surface having a high degree of uniform flatness. Base structure materials can include, for example, metals such as stainless steel, aluminum and nickel titanium memory alloys (e.g., NITINOL) as well as polymeric/plastic materials such as delrin, etc. Base structure materials can be made from, or coated with, a dielectric material. In some embodiments, the base structure is non-rigid and can be a layer of film or insulation that is used as a substrate for patterning electrical elements (e.g., electrodes, traces and the like), for example plastics such as polyimides and the like. An initial step in the methods of the invention typically includes the formation of a base substrate of the sensor. Optionally, the planar sheet of material is formed and/or disposed on a support such as a glass or ceramic plate during sensor production. The base structure can be disposed on a support (e.g., a glass plate) by PVD. This can then be followed by a sequence of photolithographic and/or chemical mask and etch steps to form the electrically conductive components. In an illustrative form, the base substrate comprises a thin film sheet of insulative material, such as a polyimide substrate that is used to pattern electrical elements. The base substrate structure may comprise one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof.

The methods of the invention include forming an electrically conductive layer on the base substrate that function as one or more sensing elements. Typically these sensing elements include electrodes, electrical conduits (e.g., traces and the like), contact pads and the like that are formed by one of the variety of methods known in the art such as photolithography, etching and rinsing to define the geometry of the active electrodes. The electrodes can then be made from electrochemically active materials having defined architectures, for example by using sputtered Pt black for the working electrode. A sensor layer such as a analyte sensing enzyme layer can then be disposed on the sensing layer by electrochemical deposition or a method other than electrochemical deposition such as spin coating, followed by vapor crosslinking, for example with a dialdehyde (glutaraldehyde) or a carbodiimide.

In an exemplary embodiment of the invention, the base substrate is initially coated with a thin film conductive layer by electrode deposition, surface sputtering, or other suitable patterning or other process step. In one embodiment this conductive layer may be provided as a plurality of thin film conductive layers, such as an initial chrome-based layer suitable for chemical adhesion to a polyimide base substrate followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base substrate. In an illustrative sensor construction designed for use as a subcutaneous glucose sensor, each sensor trace can include two or three parallel sensor elements corresponding with two or three separate electrodes such as a working electrode, a counter electrode and a reference electrode.

Embodiments of the invention include methods of adding a plurality of materials to the surface(s) of the sputtered electrode(s). One such embodiment of the invention is a method of making a sensor apparatus (e.g. a glucose sensor) for implantation within a mammal comprising the steps of: providing a base substrate; forming a conductive layer on the base substrate, wherein the conductive layer includes an electrode formed from a sputtering process that generates metallic columns of a certain architecture, forming an analyte sensing layer on the conductive layer, wherein the analyte sensing layer includes a composition that can alter the electrical current at the electrode in the conductive layer in the presence of an analyte (e.g. glucose oxidase); optionally forming a protein layer over the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer.

In the working embodiments of the invention that are disclosed herein, the analyte sensing layer comprises glucose oxidase. Optionally, the apparatus comprises an adhesion promoting layer disposed between the analyte sensing layer and the analyte modulating layer. In some embodiments of the invention, the analyte modulating layer comprises a hydrophilic comb-copolymer having a central chain and a plurality of side chains coupled to the central chain, wherein at least one side chain comprises a silicone moiety. Typically, the apparatus comprises a biocompatible material on an external surface that is adapted to contact biological tissues or fluids when implanted in vivo. In the working embodiments of the invention that are disclosed herein, the analyte sensor apparatus is an amperometric glucose sensor exhibits a highly desirable oxygen response profile. In such embodiments, the amperometric glucose sensor generates a first signal in a solution comprising 100 mg/dL glucose and 5% oxygen and a second signal in a solution comprising 100 mg/dL glucose and 0.1% oxygen (i.e., test conditions where the only substantive difference is the % oxygen), and the first signal and the second signal differ by less than 10%.

Additional functional coatings or cover layers can then be applied to an electrode or other senor element by any one of a wide variety of methods known in the art, such as spraying, dipping, etc. Some embodiments of the present invention include an analyte modulating layer deposited over an enzyme-containing layer that is disposed over a working electrode. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. Microfabrication of the underlying layers can be a factor which affects dimensional control over the analyte modulating membrane layer as well as the exact composition of the analyte limiting membrane layer material itself. In this regard, it has been discovered that several types of copolymers, for example, a copolymer of a siloxane and a nonsiloxane moiety, are particularly useful. These materials can be micro-dispensed or spin-coated to a controlled thickness. Their final architecture may also be designed by patterning and photolithographic techniques in conformity with the other discrete structures described herein.

In some embodiments of the invention, the sensor is made by methods which apply an analyte modulating layer that comprises a hydrophilic membrane coating which can regulate the amount of analyte that can contact the enzyme of the sensor layer. For example, a cover layer that is added to the glucose sensing elements of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g., Kodak AQ), hydrogels or any other membrane known to those skilled in the art that is suitable for such purposes. In certain embodiments of the invention, the analyte modulating layer comprises a hydrophilic polymer. In some embodiments of the invention, the analyte modulating layer comprises a linear polyurethane/polyurea polymer and/or a branched acrylate polymer; and/or a mixture of such polymers.

In some embodiments of the methods of invention, an adhesion promoter layer is disposed between a cover layer (e.g., an analyte modulating membrane layer) and an analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art.

The finished sensors produced by such processes are typically quickly and easily removed from a support structure (if one is used), for example, by cutting along a line surrounding each sensor on the support structure and then peeling from the support structure. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. As illustrated herein, since the base substrate is sufficiently weakly adhered directly to the underlying support, the sensors can be lifted quickly and easily peeled from the support structure, without significant further processing steps or potential damage due to stresses incurred by excessive force being applied to peel the attached sensors from the support structure. The support structure can thereafter be cleaned and reused, or otherwise discarded. The functional coating layer(s) can be applied either before or after other sensor components are removed from the support structure (e.g., by cutting).

Embodiments of the invention also include methods of sensing an analyte (e.g. glucose) within the body of a mammal (e.g. a diabetic patient), the method comprising implanting a analyte sensor embodiment disclosed herein into an in vivo environment and then sensing one or more electrical fluctuations such as alteration in current at the working electrode and correlating the alteration in current with the presence of the analyte, so that the analyte is sensed. Typically, this method comprises implanting a glucose sensor disclosed herein within the interstitial space of a diabetic individual, sensing an alteration in current at the working electrode in the presence of glucose; and then correlating the alteration in current with the presence of the glucose, so that glucose is sensed. While typical embodiments of the invention pertain to glucose sensors, the sputtered sensor electrodes disclosed herein can be adapted for use with a wide variety of devices known in the art.

As discussed in detail below, embodiments of the invention include sensor systems comprising addition elements designed to facilitate sensing of an analyte. For example, in certain embodiments of the invention, the base material comprising the sensor electrodes is disposed within a housing (e.g., a lumen of a catheter) and/or associated with other components that facilitate analyte (e.g., glucose) sensing. One illustrative sensor system comprises a processor, a base comprising a first longitudinal member and a second longitudinal member, the first and second longitudinal members each comprising at least one electrode having an electrochemically reactive surface, wherein the electrochemically reactive surface generates an electrochemical signal that is assessed by the processor in the presence of an analyte; and a computer-readable program code having instructions, which when executed cause the processor to assess electrochemical signal data obtained from the electrodes; and compute an analyte presence or concentration based upon the electrochemical signal data obtained from the electrode. Embodiments of the invention described herein can also be adapted and implemented with amperometric sensor structures, for example those disclosed in U.S. Patent Application Publication Nos. 20070227907, 200400025238, 20110319734 and 20110152654, the contents of each of which are incorporated herein by reference.

B. Illustrative Analyte Sensor Constituents and Sensor Stacks Used in Embodiments of the Invention The following disclosure provides examples of typical elements/constituents used in sensor embodiments of the invention. While these elements can be described as discrete units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g., element 402 in FIG. 1D. The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g., electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

Conductive Constituent

The electrochemical sensors of the invention typically include a conductive constituent disposed upon the base constituent that includes at least one electrode comprising a metal for contacting an analyte or its byproduct (e.g., oxygen and/or hydrogen peroxide) to be assayed (see, e.g., WE in FIG. 1A). The term "conductive constituent" is used herein according to art accepted terminology and refers to electrically conductive sensor elements such as electrodes, contact pads, traces and the like. An illustrative example of this is a conductive constituent that forms a working electrode that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 410 or a reaction product of this interaction (e.g. hydrogen peroxide). Illustrative examples of such elements include electrodes which are capable of producing variable detectable signals in the presence of variable concentrations of molecules such as hydrogen peroxide or oxygen.

In addition to the working electrode, the analyte sensors of the invention typically include a reference electrode (RE) or a combined reference and counter electrode (also termed a quasi-reference electrode or a counter/reference electrode). If the sensor does not have a counter/reference electrode then it may include a separate counter electrode (CE), which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure. In certain embodiments of the invention, the reactive surfaces of the electrodes are of different relative areas/sizes, for example a 1× reference electrode, a 3.2× working electrode and a 6.3× counter electrode.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant applied potential. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g., by excluding interfering species of a specific size). Examples of interference rejection constituents include one or more layers or coatings of compounds such as hydrophilic polyurethanes, cellulose acetate (including cellulose acetate incorporating agents such as poly(ethylene glycol), polyethersulfones, polytetra-fluoroethylenes, the perfluoronated ionomer Nafion™, polyphenylenediamine, epoxy and the like.

Analyte Sensing Constituent

The electrochemical sensors of the invention include an analyte sensing constituent disposed on the electrodes of the sensor (see, e.g., element 410 in FIG. 1H). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard, the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g., oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g., glucose oxidase) that has been combined with a second protein (e.g., albumin) in a fixed ratio (e.g., one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g., the body of a mammal) and generates hydrogen peroxide.

As noted above, the enzyme and the second protein (e.g., an albumin) are typically treated to form a crosslinked matrix (e.g., by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde. Other suitable cross-linkers also may be used, as will be evident to those skilled in the art.

As noted above, in some embodiments of the invention, the analyte sensing constituent includes an agent (e.g., glucose oxidase) capable of producing a signal (e.g., a change in oxygen and/or hydrogen peroxide concentrations) that can be sensed by the electrically conductive elements (e.g., electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

Protein Constituent

The electrochemical sensors of the invention optionally include a protein constituent disposed between the analyte sensing constituent and the analyte modulating constituent (see, e.g., element 416 in FIG. 1H). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g., element 414 in FIG. 1H). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as 3-aminopropyltrimethoxysilane.

Analyte Modulating Constituent

The electrochemical sensors of the invention include an analyte modulating constituent disposed on the sensor (see, e.g., element 412 in FIG. 1H). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally, such analyte modulating constituents can be formed to prevent or restrict the diffusion of one type of molecule through the constituent (e.g., glucose), while at the same time allowing or even facilitating the diffusion of other types of molecules through the constituent (e.g., O2).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The analyte modulating sensor membrane assembly serves several functions, including selectively allowing the passage of glucose therethrough (see, e.g., U.S. Patent Application No. 2011-0152654).

Cover Constituent

The electrochemical sensors of the invention include one or more cover constituents, which are typically electrically insulating protective constituents (see, e.g., element 406 in FIG. 1B). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imagable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

FIG. 1B illustrates a cross-section of a typical sensor embodiment 400 of the present invention that includes constituents discussed above. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 1B. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 1B includes a base substrate layer 402 to support the sensor 400. The base substrate layer 402 can be made of a material such as a metal and/or a ceramic and/or a polymeric substrate, which may be self-supporting or further supported by another material as is known in the art. Embodiments of the invention include a conductive layer 404 which is disposed on and/or combined with the base substrate layer 402. Typically, the conductive layer 404 comprises one or more electrically conductive elements that function as electrodes. An operating sensor 400 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 402 and/or conductive layer 404 can be generated using many known techniques and materials. In certain embodiments of the invention, the electrical circuit of the sensor is defined by etching the disposed conductive layer 404 into a desired pattern of conductive paths. A typical electrical circuit for the sensor 400 comprises two or more adjacent conductive paths with regions at a proximal end to form contact pads and regions at a distal end to form sensor electrodes. An electrically insulating cover layer 406 such as a polymer coating can be disposed on portions of the sensor 400. Acceptable polymer coatings for use as the insulating protective cover layer 406 can include, but are not limited to, non-toxic biocompatible polymers such as silicone compounds, polyimides, biocompatible solder masks, epoxy acrylate copolymers, or the like. In the sensors of the present invention, one or more exposed regions or apertures 408 can be made through the cover layer 406 to open the conductive layer 404 to the external environment and to, for example, allow an analyte such as glucose to permeate the layers of the sensor and be sensed by the sensing elements. Apertures 408 can be formed by a number of techniques, including laser ablation, tape masking, chemical milling or etching or photolithographic development or the like. In certain embodiments of the invention, during manufacture, a secondary photoresist can also be applied to the protective layer 406 to define the regions of the protective layer to be removed to form the aperture(s) 408. The exposed electrodes and/or contact pads can also undergo secondary processing (e.g., through the apertures 408), such as additional plating processing, to prepare the surfaces and/or strengthen the conductive regions.

In the sensor configuration shown in FIG. 1B, an analyte sensing layer 410 is disposed on one or more of the exposed electrodes of the conductive layer 404. Typically, the analyte sensing layer 410 is an enzyme layer. Most typically, the analyte sensing layer 410 comprises an enzyme capable of producing and/or utilizing oxygen and/or hydrogen peroxide, for example the enzyme glucose oxidase. Optionally, the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 410 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can be monitored by any one of a variety of sensor detector apparatuses such as a universal sensor amperometric biosensor detector or one of the variety of similar devices known in the art such as glucose monitoring devices produced by Medtronic Diabetes.

In embodiments of the invention, the analyte sensing layer 410 can be applied over portions of the conductive layer or over the entire region of the conductive layer. Typically the analyte sensing layer 410 is disposed on the working electrode which can be the anode or the cathode. Optionally, the analyte sensing layer 410 is also disposed on a counter and/or reference electrode. Methods for generating a thin analyte sensing layer 410 include brushing the layer onto a substrate (e.g., the reactive surface of a platinum black electrode), as well as spin coating processes, dip and dry processes, low shear spraying processes, ink-jet printing processes, silk screen processes and the like. In certain embodiments of the invention, brushing is used to: (1) allow for a precise localization of the layer; and (2) push the layer deep into the architecture of the reactive surface of an electrode (e.g., platinum black produced by a sputtering process).

Typically, the analyte sensing layer 410 is coated and or disposed next to one or more additional layers. Optionally, the one or more additional layers includes a protein layer 416 disposed upon the analyte sensing layer 410. Typically, the protein layer 416 comprises a protein such as human serum albumin, bovine serum albumin or the like. Typically, the protein layer 416 comprises human serum albumin. In some embodiments of the invention, an additional layer includes an analyte modulating layer 412 that is disposed above the analyte sensing layer 410 to regulate analyte contact with the analyte sensing layer 410. For example, the analyte modulating membrane layer 412 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g., Kodak AQ), hydrogels or any other suitable hydrophilic membranes known to those skilled in the art.

In certain embodiments of the invention, an adhesion promoter layer 414 is disposed between the analyte modulating layer 412 and the analyte sensing layer 410 as shown in FIG. 1H in order to facilitate their contact and/or adhesion. In a specific embodiment of the invention, an adhesion promoter layer 414 is disposed between the analyte modulating layer 412 and the protein layer 416 as shown in FIG. 1B in order to facilitate their contact and/or adhesion. The adhesion promoter layer 414 can be made from any one of a wide variety of materials known in the art to facilitate the bonding between such layers. Typically, the adhesion promoter layer 414 comprises a silane compound. In alternative embodiments, protein or like molecules in the analyte sensing layer 410 can be sufficiently crosslinked or otherwise prepared to allow the analyte modulating membrane layer 412 to be disposed in direct contact with the analyte sensing layer 410 in the absence of an adhesion promoter layer 414.

C. Typical System Embodiments of the Invention

A specific illustrative system embodiment consists of a glucose sensor comprising the electrode configurations as disclosed herein, a transmitter and receiver and a glucose meter. In this system, radio signals from the transmitter can be sent to the pump receiver at regular time periods (e.g., every 5 minutes) to provide real-time sensor glucose (SG) values. Values/graphs can be displayed on a monitor of the pump receiver so that a user can self-monitor blood glucose and deliver insulin using their own insulin pump. Typically the sensor systems disclosed herein can communicate with other medical devices/systems via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g., an insulin pump). Typically in such devices, the physiological characteristic values include a plurality of measurements of blood glucose.

Figure 2:
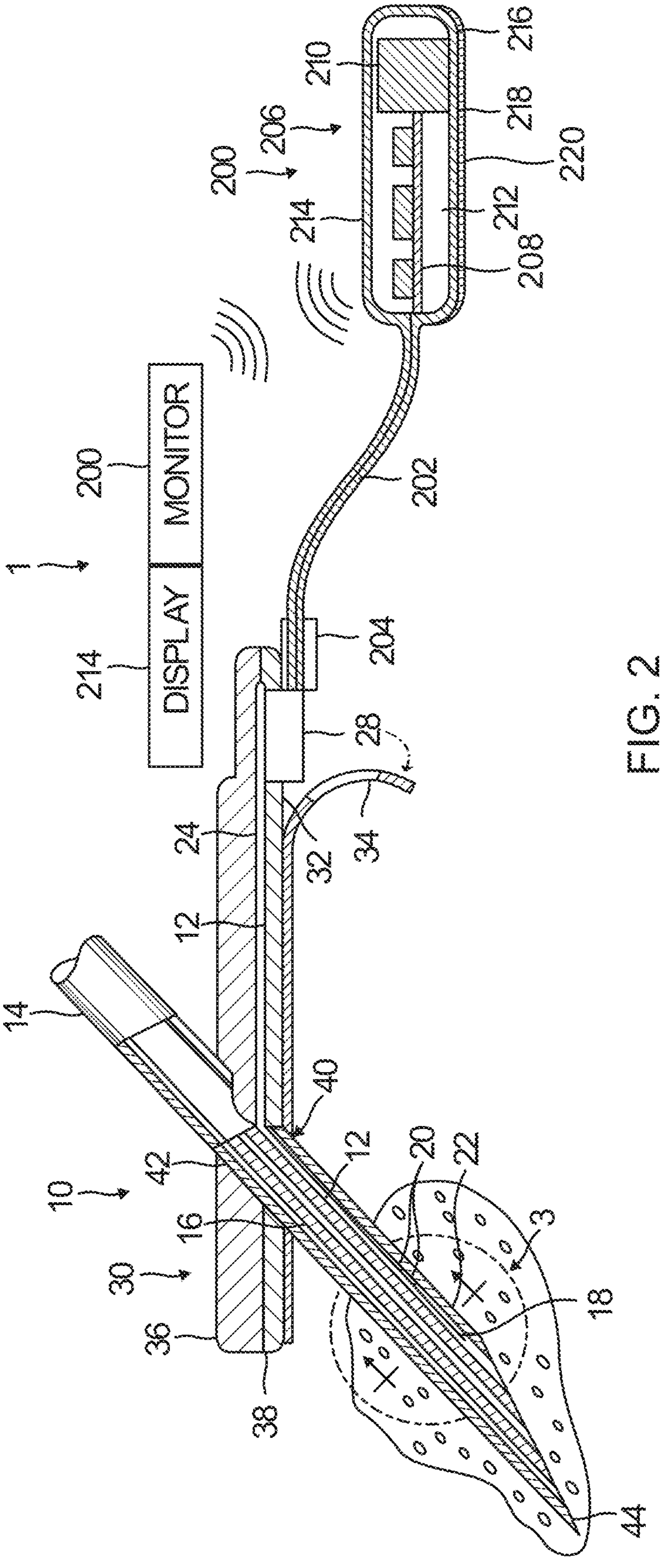
FIG. 2 provides a perspective view illustrating one type of subcutaneous sensor insertion set, a telemetered characteristic monitor transmitter device, and a data receiving device, elements that can be adapted for use with embodiments of the invention.

FIG. 2 provides a perspective view of one generalized embodiment of subcutaneous sensor insertion system that can be adapted for use with the sensor electrodes disclosed herein and a block diagram of a sensor electronics device according to one illustrative embodiment of the invention. Additional elements typically used with such sensor system embodiments are disclosed for example in U.S. patent application No. 20070163894, the contents of which are incorporated by reference. FIG. 2 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The base is designed so that the sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 200 by a connector block 28 (or the like) as shown and described in U.S. Pat. No. 5,482,473, entitled FLEX CIRCUIT CONNECTOR, which is incorporated by reference.

As shown in FIG. 2, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 200 is coupled to a sensor set 10 by a cable 402 through a connector 24 that is electrically coupled to the connector block 28 of the connector portion 24 of the sensor set 10.

In the embodiment shown in FIG. 2, the telemetered characteristic monitor 400 includes a housing 206 that supports a printed circuit board 208, batteries 210, antenna 212, and the cable 202 with the connector 204. In some embodiments, the housing 206 is formed from an upper case 214 and a lower case 216 that are sealed with an ultrasonic weld to form a waterproof (or resistant) seal to permit cleaning by immersion (or swabbing) with water, cleaners, alcohol or the like. In some embodiments, the upper and lower case 214 and 216 are formed from a medical grade plastic. However, in alternative embodiments, the upper case 214 and lower case 216 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 216 may have an underside surface coated with a suitable pressure sensitive adhesive layer 218, with a peel-off paper strip 220 normally provided to cover and protect the adhesive layer 218, until the sensor set telemetered characteristic monitor transmitter 200 is ready for use.

In the illustrative embodiment shown in FIG. 2, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. Nos. 4,562,751; 4,678,408; 4,685,903 or 4,573,994, to control delivery of insulin to a diabetic patient.

In the illustrative embodiment shown in FIG. 2, the sensor electrodes 10 may be used in a variety of sensing applications and may be configured in a variety of positions on a base structure and further be formed to include materials that allow a wide variety of functions. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 2, the monitor of sensor signals 200 may also be referred to as a sensor electronics device 200. The monitor 200 may include a power source, a sensor interface, processing electronics (i.e., a processor), and data formatting electronics. The monitor 200 may be coupled to the sensor set 10 by a cable 402 through a connector that is electrically coupled to the connector block 28 of the connection portion 24. In an alternative embodiment, the cable may be omitted. In this embodiment of the invention, the monitor 200 may include an appropriate connector for direct connection to the connection portion 24 of the sensor set 10. The sensor set 10 may be modified to have the connector portion 24 positioned at a different location, e.g., on top of the sensor set to facilitate placement of the monitor 200 over the sensor set.

As noted above, embodiments of the sensor elements and sensors can be operatively coupled to a variety of other system elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Figure 3:
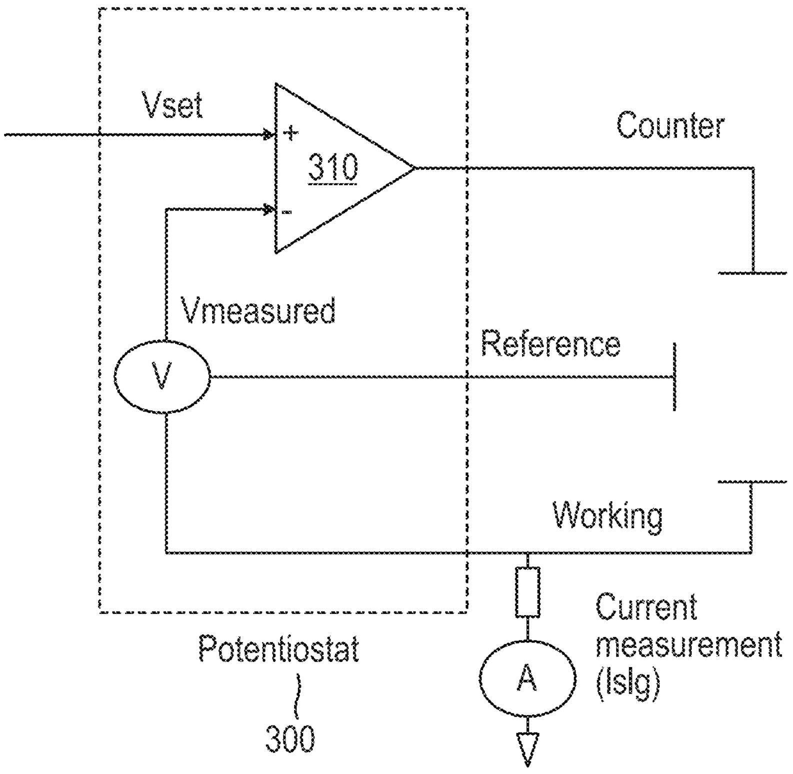
FIG. 3 shows a schematic of a potentiostat that may be used to measure current in embodiments of the present invention.

FIG. 3 shows a schematic of a potentiostat that may be used to measure current in embodiments of the present invention. As shown in FIG. 3, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (Isig) that is output from the potentiostat.

Illustratively, if the voltage set at the reference electrode is maintained at a fixed voltage (e.g., 0.5 volts), the amount of current flowing from the counter electrode to a working electrode has a fairly linear relationship with unity slope to the amount of oxygen present in the area surrounding the enzyme and the electrodes. Thus, increased accuracy in determining an amount of oxygen in the blood may be achieved by maintaining the reference electrode at the fixed voltage and utilizing this region of the current-voltage curve for varying levels of blood oxygen.

In one or more examples, the op amp, utilizing feedback through the sensor electrodes, attempts to maintain a prescribed voltage between a reference electrode and a working electrode by adjusting the voltage at a counter electrode. Current may then flow from a counter electrode to a working electrode. Such current may be measured to ascertain the electrochemical reaction between the sensor electrodes and the biomolecule of a sensor that has been placed in the vicinity of the sensor electrodes and used as a catalyzing agent. Further examples of operation can be found in U.S. Pat. No. 9,632,060 which patent is incorporated by reference herein. In one or more examples, voltages applied to the electrodes allow measurement of the concentration of the analyte using the electrical current and Electrochemical Impedance Spectroscopy (EIS).

Embodiments of the invention include devices which process display data from measurements of a sensed physiological characteristic (e.g., blood glucose concentrations) in a manner and format tailored to allow a user of the device to easily monitor and, if necessary, modulate the physiological status of that characteristic (e.g., modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g., a glucose sensor).

An illustrative system embodiment consists of a glucose sensor, a transmitter and pump receiver and a glucose meter.

In this system, radio signals from the transmitter can be sent to the pump receiver every 5 minutes to provide real-time sensor glucose (SG) values. Values/graphs are displayed on a monitor of the pump receiver so that a user can self-monitor blood glucose and deliver insulin using their own insulin pump. Typically, an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g., an insulin pump). Typically in such devices, the physiological characteristic values include a plurality of measurements of blood glucose.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle car fluid, joint fluid, gastric aspirate or the like. In addition, solid or desiccated samples may be dissolved in an appropriate solvent to provide a liquid mixture suitable for analysis.

EXAMPLES

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The descriptions and specific examples, while indicating some embodiments of the present invention are given by way of illustration and not limitation. Many changes and modifications within the scope of the present invention may be made without departing from the spirit thereof, and the invention includes all such modifications.

First Example: Detection of Conduction Path

Figure 4:
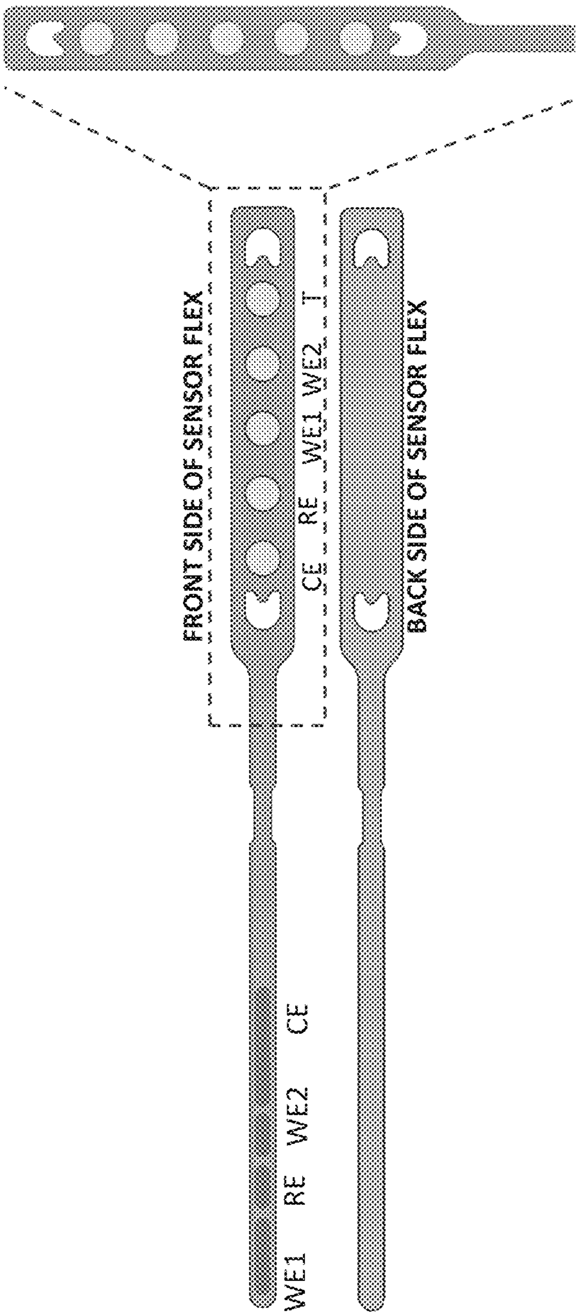
FIG. 4 illustrates a sensor portion according to a first example.
Figure 5A:
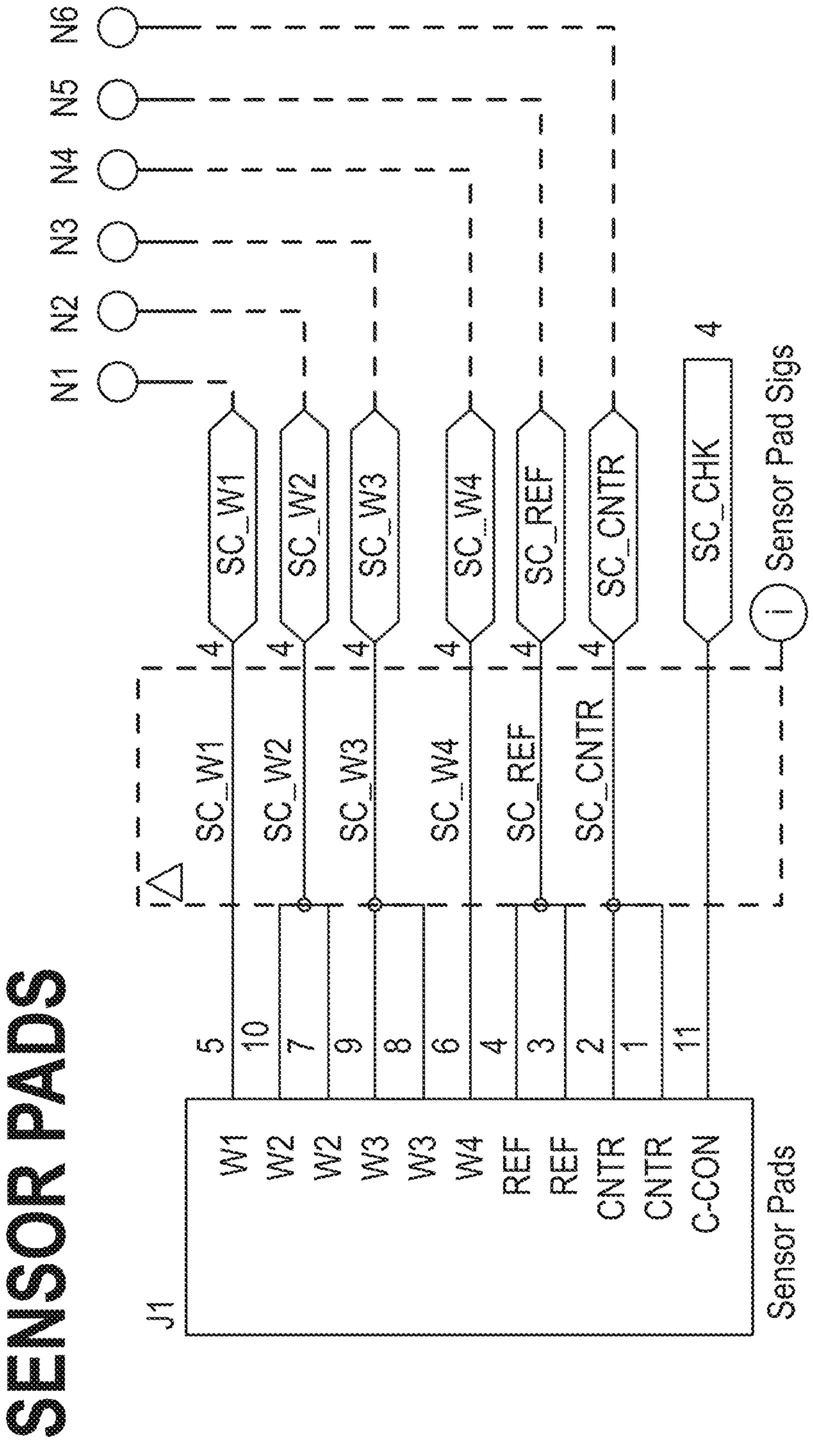
FIG. 5A illustrates sensor pad connections on the sensor portion according to the first example.
Figure 5B:
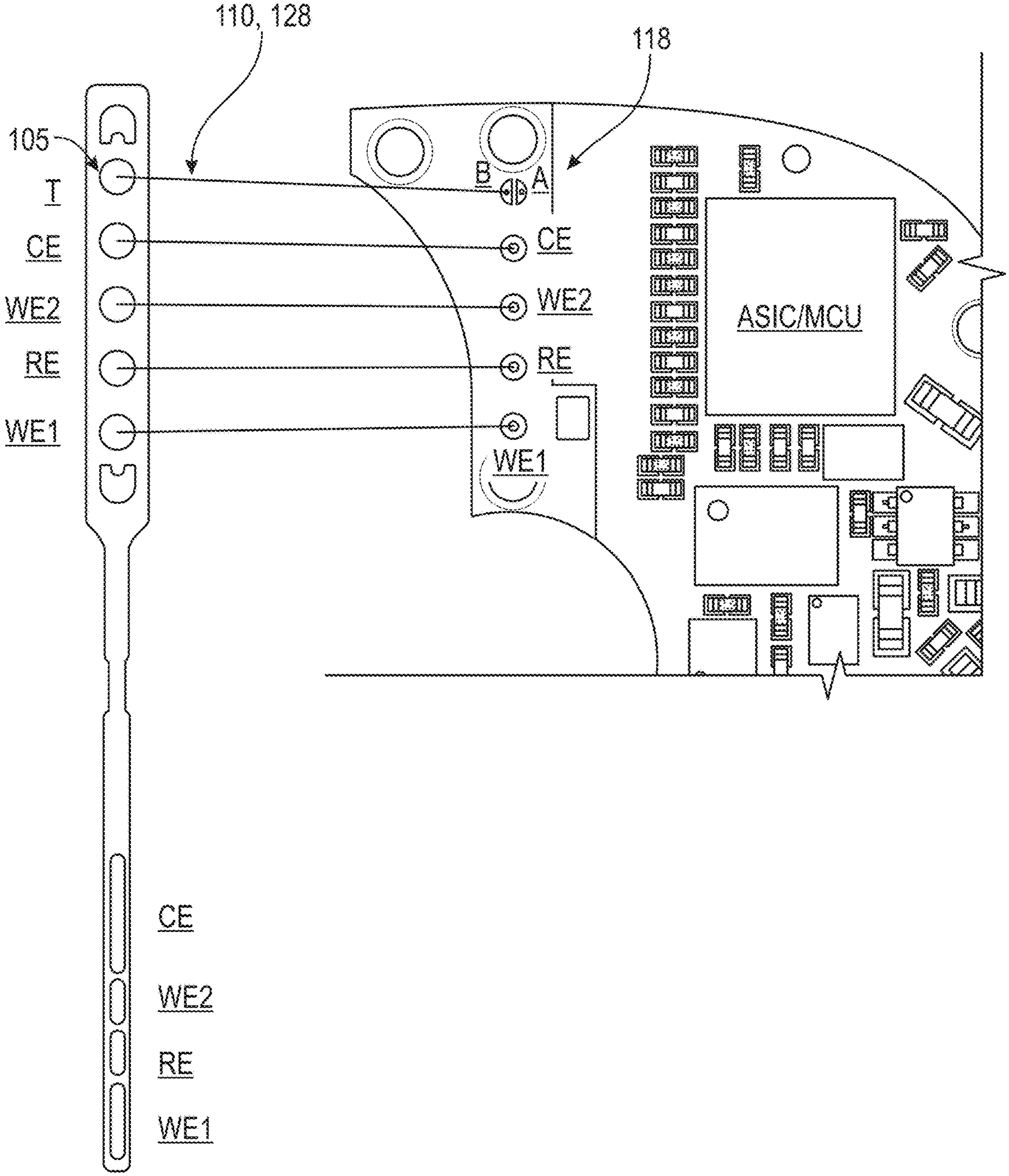
FIG. 5B illustrates the electrical connection between the PCBA and the sensor portion according to the first example.
Figure 5C:
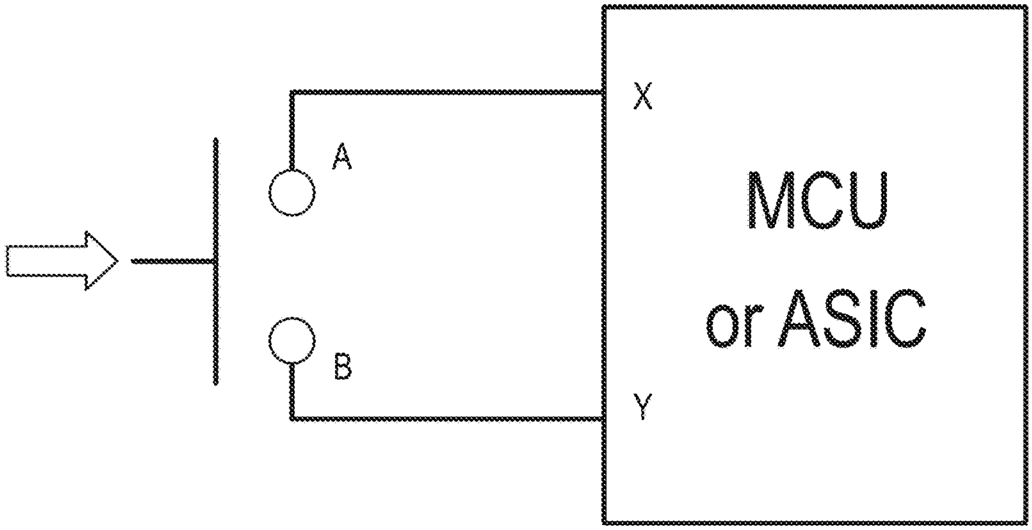
FIG. 5C illustrates the circuit detecting the electrical connection according to the first example.

FIG. 4 illustrates an example wherein the sensing portion comprises one or more working electrodes WE1, WE2, a counter electrode CE, a reference electrode RE, and a plurality of contacts 105 including first contact T. FIGS. 5A-5C illustrate the electrical connection between the PCBA and the electrodes on the sensing portion when the elastomer mates, presses, or attaches the proximal end of the sensor portion onto the PCBA to make physical contact and electrical contact between the contacts 105 and the sensor connection contacts 118.

Figure 6A:
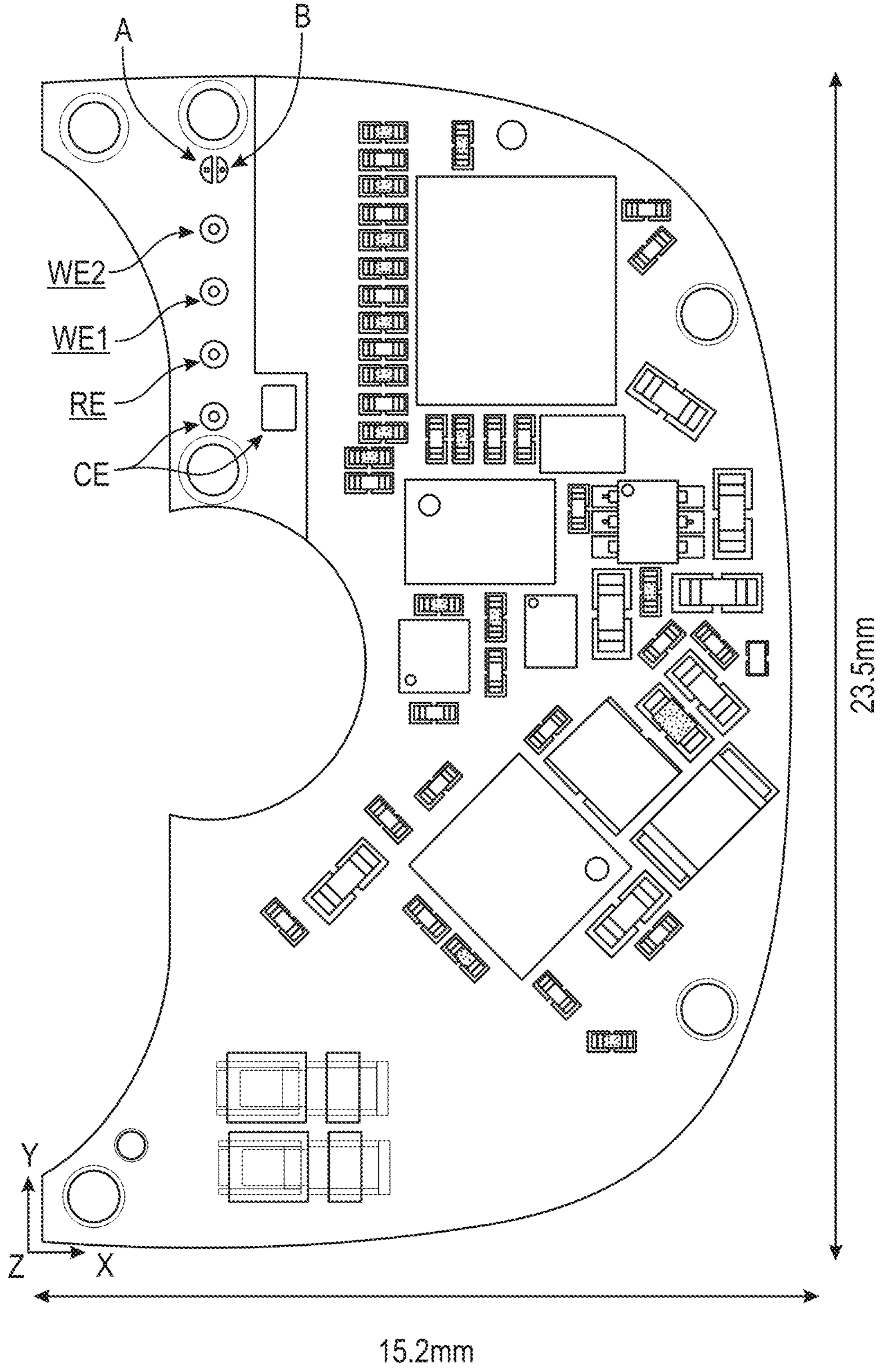
FIG. 6A illustrates sensor connection pads on the PCBA according to a first configuration of the first example.

FIGS. 6A-6F illustrate example configurations of the sensor connections contacts 118 on the PCBA for connection to the electrodes CE, RE, WE1, WE2 on the sensing portion via contacts 105. FIG. 6A illustrates the sensor connection contacts 118 include a second contact A and a third contact B and the one or more processors comprise an application specific integrated circuit (ASIC) having an output connected to the second contact A. The output outputs the voltage V applied to an electrode. In one or more examples, the output applies the voltage V to the electrode comprising a counter electrode or reference electrode so as to establish the reference potential of the environment via the reference electrode.

FIG. 5C illustrates that the sensor portion in operable connection with the PCBA causes the first contact T to physically contact both the second contact A and the contact B so as to form the electrical connection between the second contact A and the third contact pad B. The processor (e.g., ASIC) in the circuit 128 detects the electrical connection 110 by measuring a conduction path (e.g., the electrical short) between the second contact A and the third contact B. The operable connection of the sensor portion also connects the electrodes WE1, WE2, RE, and CE to the ASIC through physical contact between the WE1, WE2, RE, and CE contacts 105 (on the sensor portion) and the WE1, WE2, RE, and CE sensor connection contacts 118 on the PCBA, respectively. In one or more examples, the circuit 128 detecting the electrical connection 110 comprises the first contact T, the second contact A, the third contact B, and optionally the processor 108 (e.g., ASIC or MCU) as illustrated in FIG. 5C. In one or more examples, the circuit 128 detecting the electrical connection 110 comprises the first contact T, the second contact A, the third contact B, and optionally node X and node Y on the processor 108. In one or more examples, node X is an output applying a voltage V and node Y is an input sensing a voltage to detect the electrical connection 110. In one or more examples, the electrical connection 110 when the sensor portion is operably connected to the PCBA is characterized by a potential difference between the second contact (A) and the third contact (B) (or between nodes X and Y) being less than 10% of the voltage V applied by the circuit (by node X) to the second contact (A).

Figure 6B:
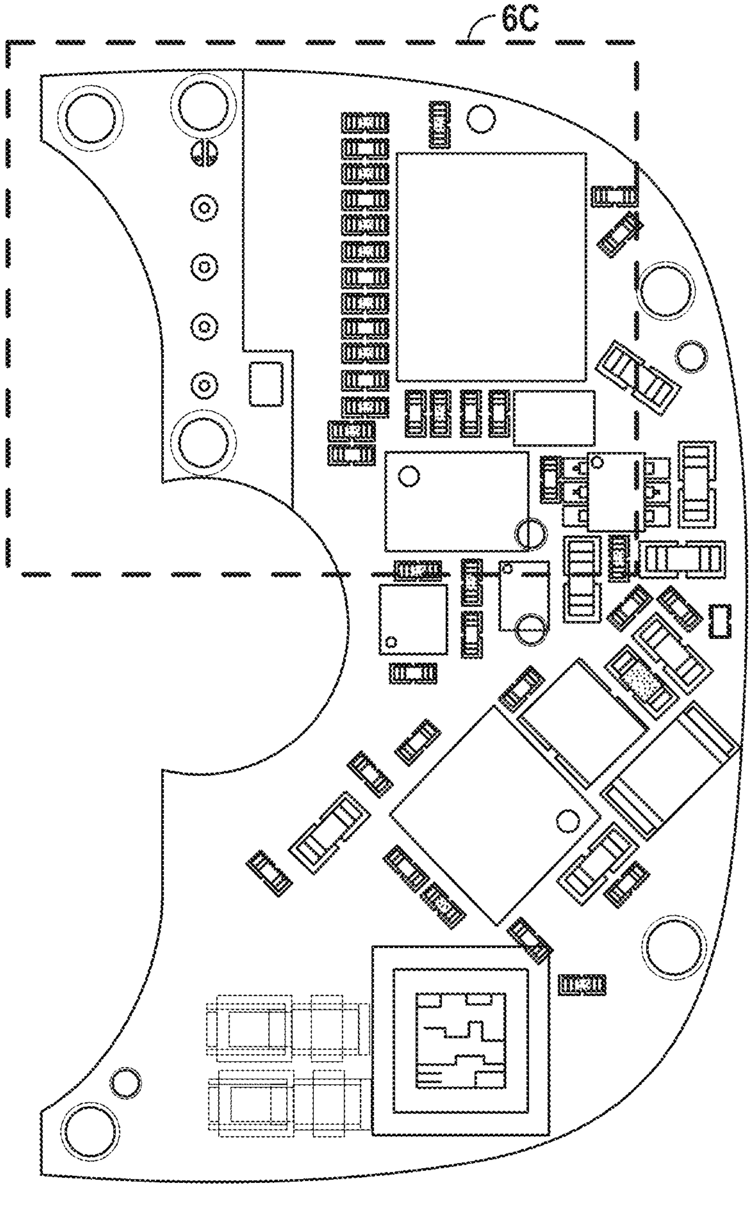
FIG. 6B is an alternate view of FIG. 6A
Figure 6C:
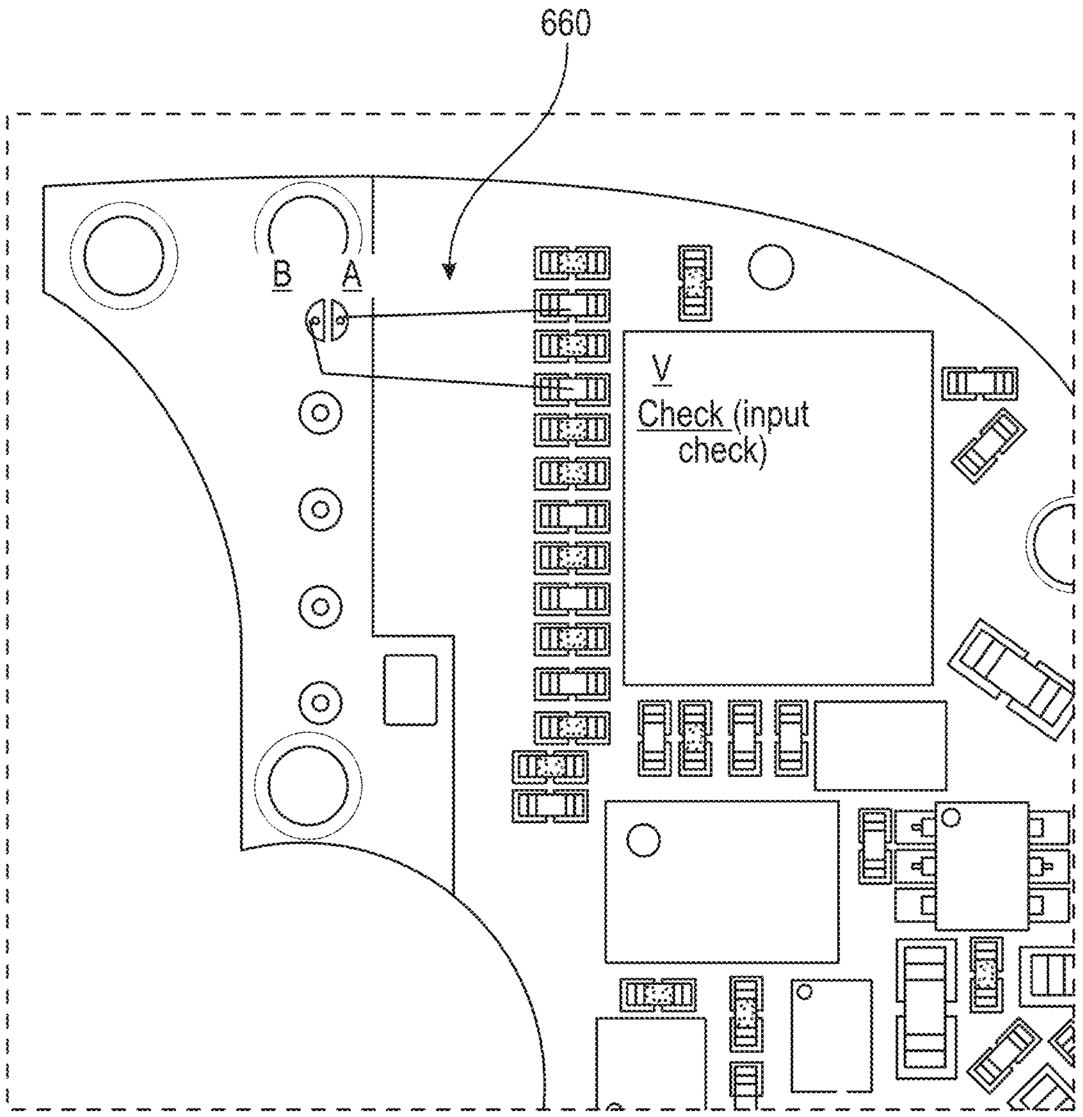
FIG. 6C is a close-up view of the sensor connection pads in FIG. 6B showing connection to the ASIC.

FIGS. 6A-6C illustrate an example wherein the counter electrode pad (CNTR) is split such that half of the pad (the COUNTER half-pad, SC_CNTR, or second contact A) is connected to the counter electrode output (V) of the ASIC and the counter electrode CE, while the other half of the pad (the monitoring half-pad, CNTR_CHK, or third contact B) is connected to an analog input or digital check input of the ASIC. If the sensor portion is connected to the PCBA such that the contact T shorts the split contacts A and B together, the signal at SC_CNTR (second contact A) appears at the monitoring half-pad (CNTR_CHK, third contact B), thus enabling detection of the electrical connection to between the sensor portion and the PCBA. FIG. 6C illustrates the PCBA comprises conductive tracks 660 for connecting contacts A and B to the output (V) and check input of the ASIC.

Second Example: Contacts on Front Side of Sensor Portion

Figure 6D:
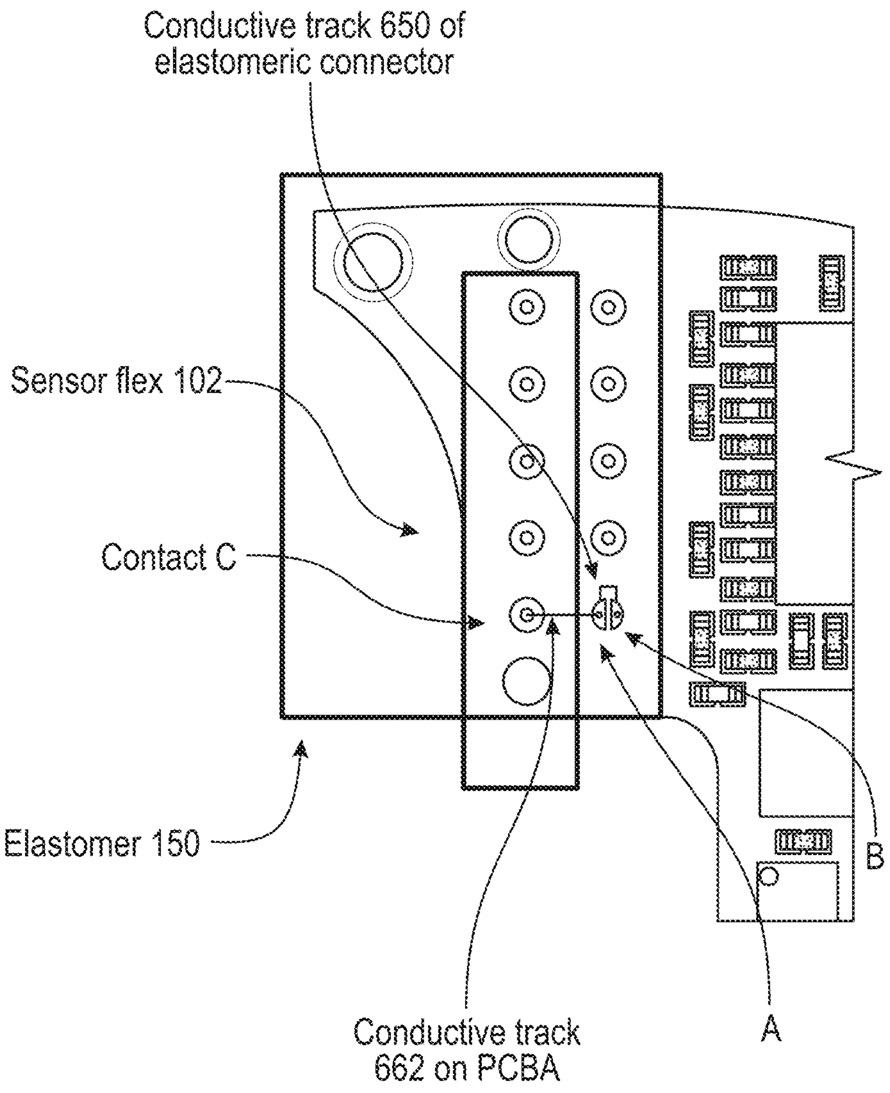
FIG. 6D illustrates sensor connection pads on the PCBA according to a second configuration of the first example.

FIG. 6D illustrate another embodiment wherein a front side of the sensor portion faces and is in physical contact with the PCBA.

The sensor includes the contacts comprising a first contact (T), and the PCBA includes the sensor connection contacts comprising a second contact (A), a third contact (B), and a fourth contact (C). The PCBA further includes a first conductive track electrically 662 connecting the second contact (A) to the fourth contact (C).

The analyte sensor apparatus further includes an elastomer connector 150 comprising a second conductive track 650. The sensor portion 102 in operable connection with the PCBA comprises:

(1) the elastomer connector 150 pressing the first contact (T) into physical and electrical contact with the fourth contact (C).

(2) the second conductive track 650 electrically connecting to the second contact (A) to the third contact (B), and (3) the first conductive track 662 and the second conductive track 650 forming the electrical connection 110 between the fourth contact (C), the third contact (B), the second contact (A) and the first contact (T).

The circuit 128 detects the electrical connection comprising a conduction path (e.g., electrical short) between the second contact (A) and the third contact (B), e.g., by the ASIC measuring a conductive path e.g., short between output V and input check on the ASIC as illustrated in FIG. 6C. In or more examples, the circuit measures the conductive path between contact C and contact B.

In one or more examples, the circuit 128 detecting the electrical connection 110 comprises the first contact T, the second contact A, the third contact B, the fourth contact (C), the first conductive track, the second conductive track, and output V and input check (e.g., on the processor 108). In one or more examples, the electrical connection 110 when the sensor portion is operably connected to the PCBA is characterized by a potential difference between the second contact (A) and the third contact (B) (or between output V and input check) being less than 10% of the voltage V applied by the circuit (by output V) to the second contact (A). Input check senses the voltage to determine the potential difference.

Third Example: Contacts on Back Side and Front Side of Sensor Portion

Figure 6E:
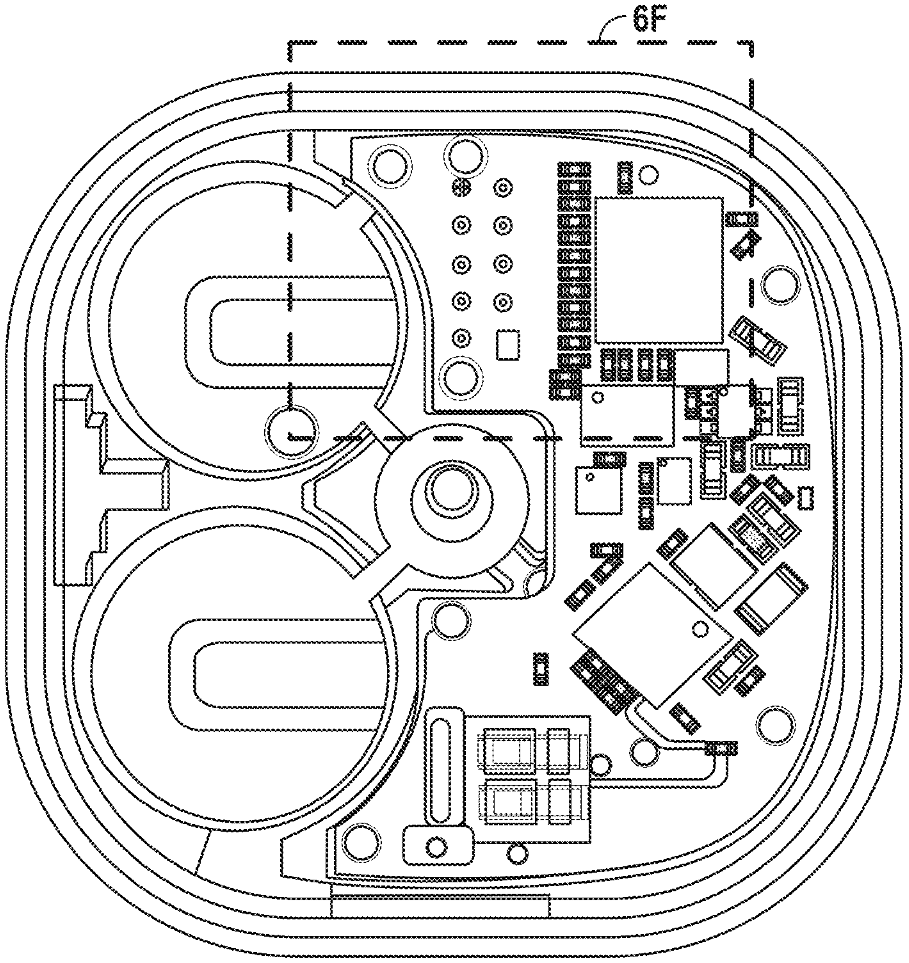
FIG. 6E illustrates positioning of the PCBA in a housing.
Figure 6F:
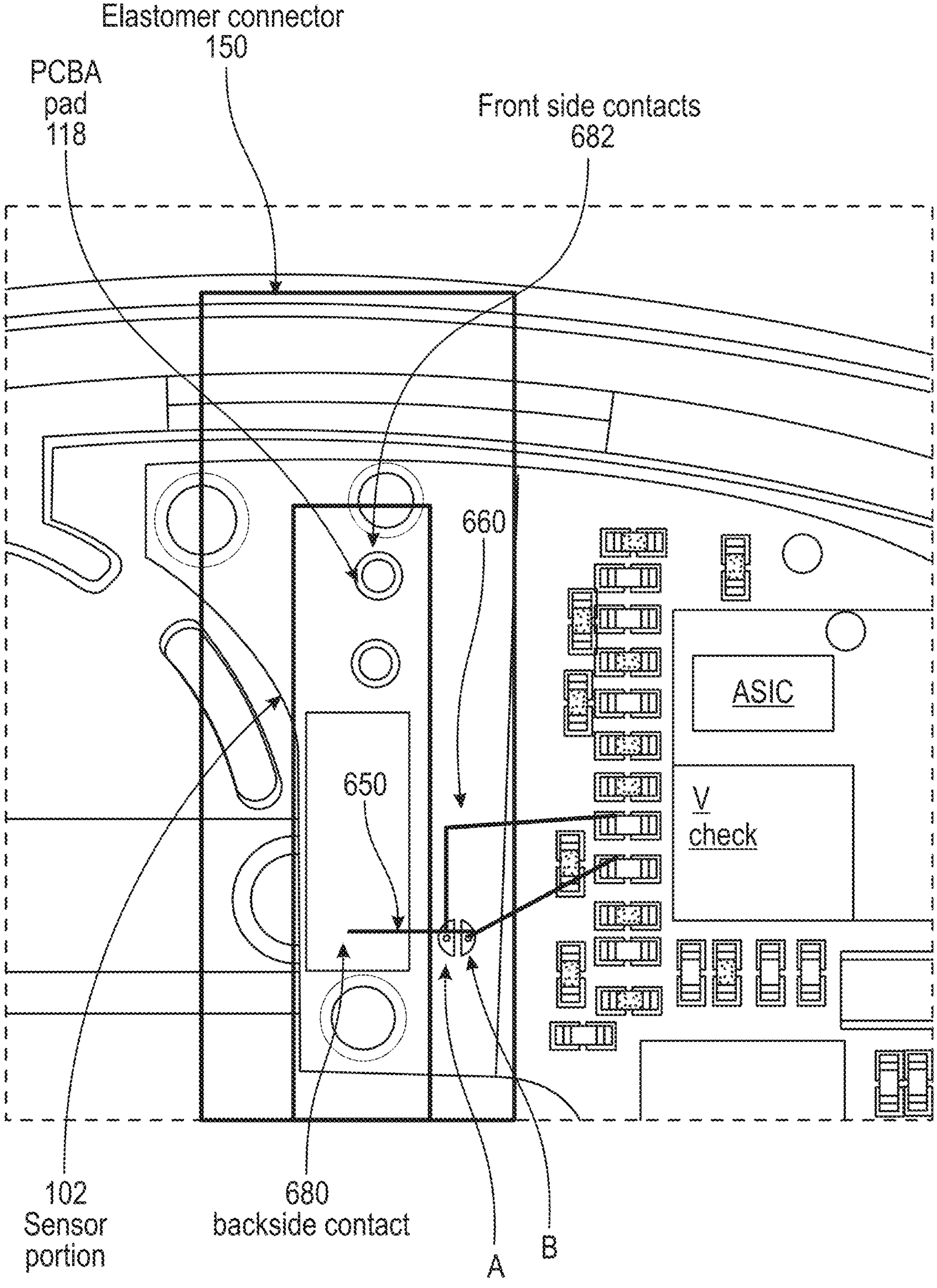
FIG. 6F is a close up view of FIG. 6E.

FIGS. 6E and 6F further illustrates an embodiment wherein the sensor portion includes contacts 682 on a front side of the sensor portion facing the PCBA and at least one contact (first contact 680) on the back side of the sensor portion facing away from the PCBA.

The apparatus includes an elastomer connector 150 including a conductive track 650 and the PCBA comprises a plurality of sensor connection contacts including a second contact (A) and a third contact (B).

The sensor portion in operable connection with the PCBA comprises the conductive track 650 forming the electrical connection 110 between the first contact 680, the second contact (A), and the third contact (B). In one or more examples the first contact 680 on the back side forms the electrical connection applying a voltage (V) to the one of the electrodes comprising a counter electrode.

The circuit 128 detects the electrical connection 110 by measuring the conduction path between the second contact A and the third contact B.

In one or more examples, the circuit 128 detecting the electrical connection 110 comprises the first contact 680, the second contact A, the third contact B, conductive track 650, and output V and input check (e.g., on the processor 108). In one or more examples, the electrical connection 110 when the sensor portion is operably connected to the PCBA is characterized by a potential difference between the second contact (A) and the third contact (B) (or between output V and input check) being less than 10% of the voltage V applied by the circuit (by output V) to the second contact (A). Input check senses the voltage at input check to determine the potential difference.

Figure 6G:
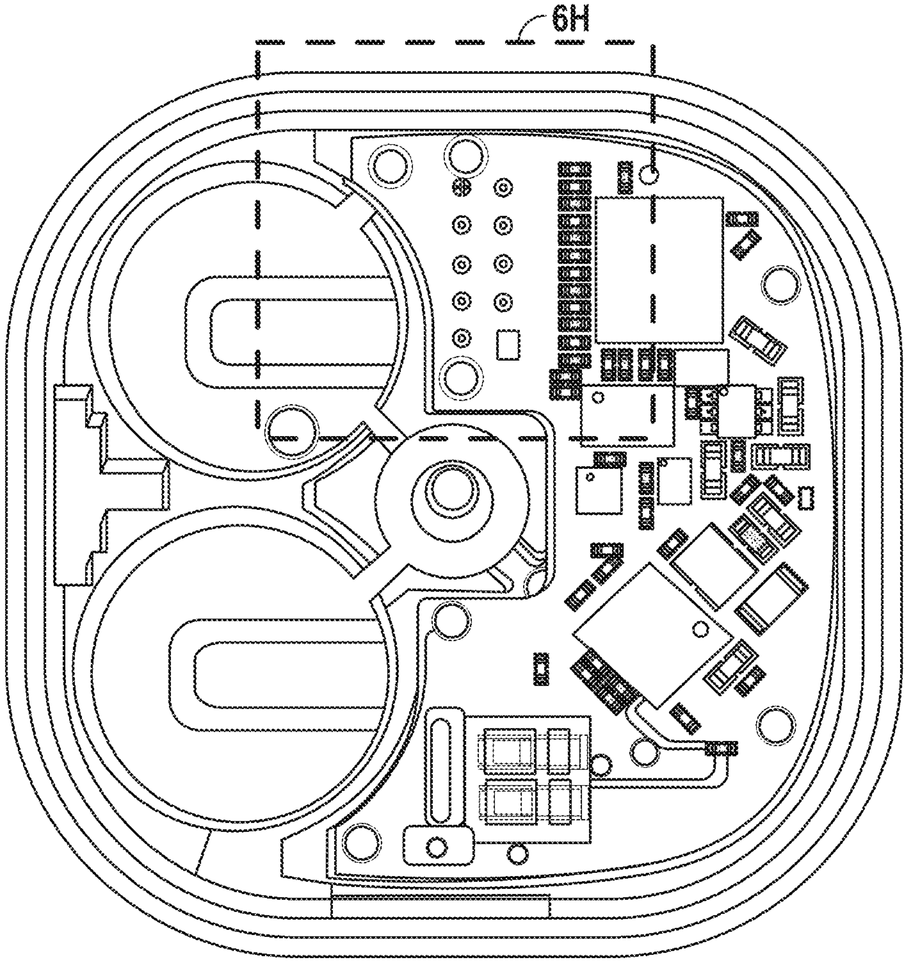
FIG. 6G illustrates an analyte sensor apparatus according to a third configuration of the first example.
Figure 6H:
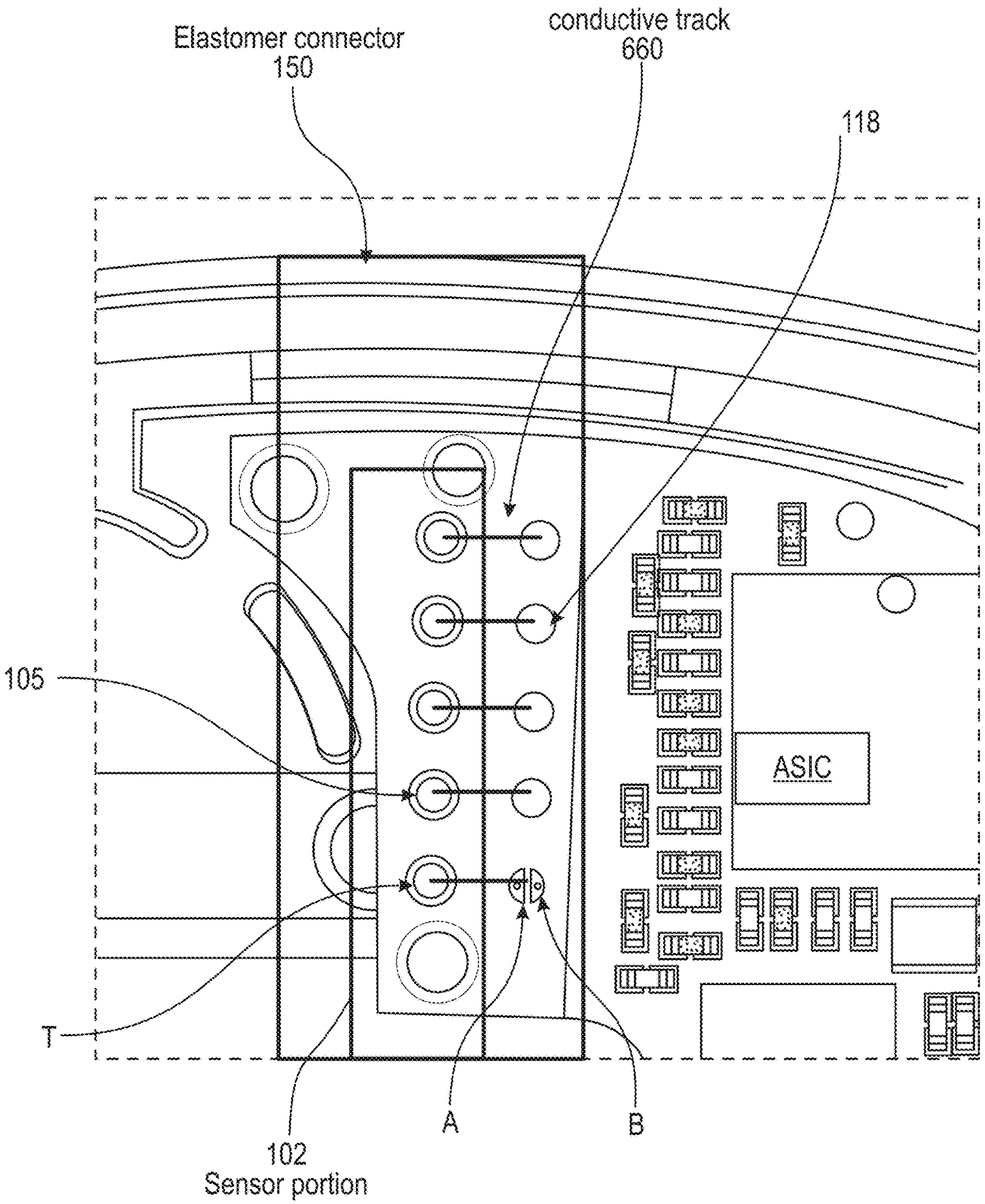
FIG. 6H is a close up view of the third configuration of FIG. 6G.

Fourth Example: Sensor Portion Attached to PCBA with Contacts Facing Away from PCBA FIG. 6G and FIG. 6H illustrate contacts on the sensor portion facing away from the PCBA when the sensor portion is clamped to the PCBA using an elastomeric connector 150 comprising a plurality of conductive tracks 660.

The PCBA comprises a plurality of sensor connection contacts 118 including the second contact (A) and the third contact (B) and the contacts 105 including first contact T electrically connect the electrodes to the PCBA.

The sensor portion in operable connection with the PCBA comprises:

(1) each of the conductive tracks 660 electrically connecting one of the contacts 105 to one of the plurality of sensor connection contacts 118, and (2) one of the conductive tracks forming the electrical connection 110 between the first contact (T), the second contact (A), and the third contact (B).

The circuit 128 detects the electrical connection 110 by measuring the conduction path between the second contact A and the third contact B.

In one or more examples, the circuit 128 detecting the electrical connection 110 comprises the first contact T, the second contact A, the third contact B, one of the conductive tracks 660, and output V and input check (e.g., on the processor 108). In one or more examples, the electrical connection 110 when the sensor portion is operably connected to the PCBA is characterized by a potential difference between the second contact (A) and the third contact (B) (or between output V and input check) being less than 10% of the voltage V applied by the circuit (by output V) to the second contact (A). Input check senses the voltage at input check to determine the potential difference.

Thus, in one or more ore embodiments of the first example, the second example, the third example, and the fourth example, a proper electrical connection 110 is present when the conduction path is characterized by a potential difference between the second contact (A) and the third contact (B) being less than 10% of a voltage applied by the circuit 128 to the second contact (A) or the third contact (B) so as to measure the electrical connection 110.

Fifth Example: Voltage Divider

Figure 7:
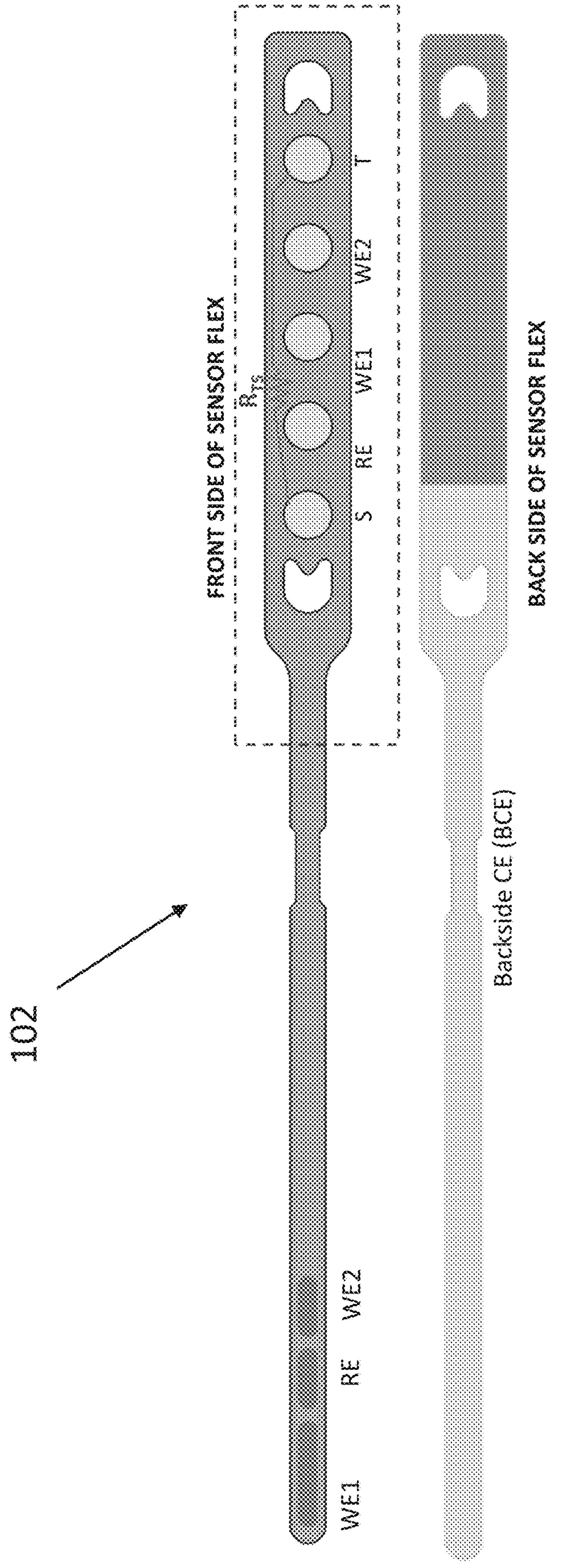
FIG. 7 illustrates a sensor portion according to an example implementing a voltage divider.
Figure 8A:
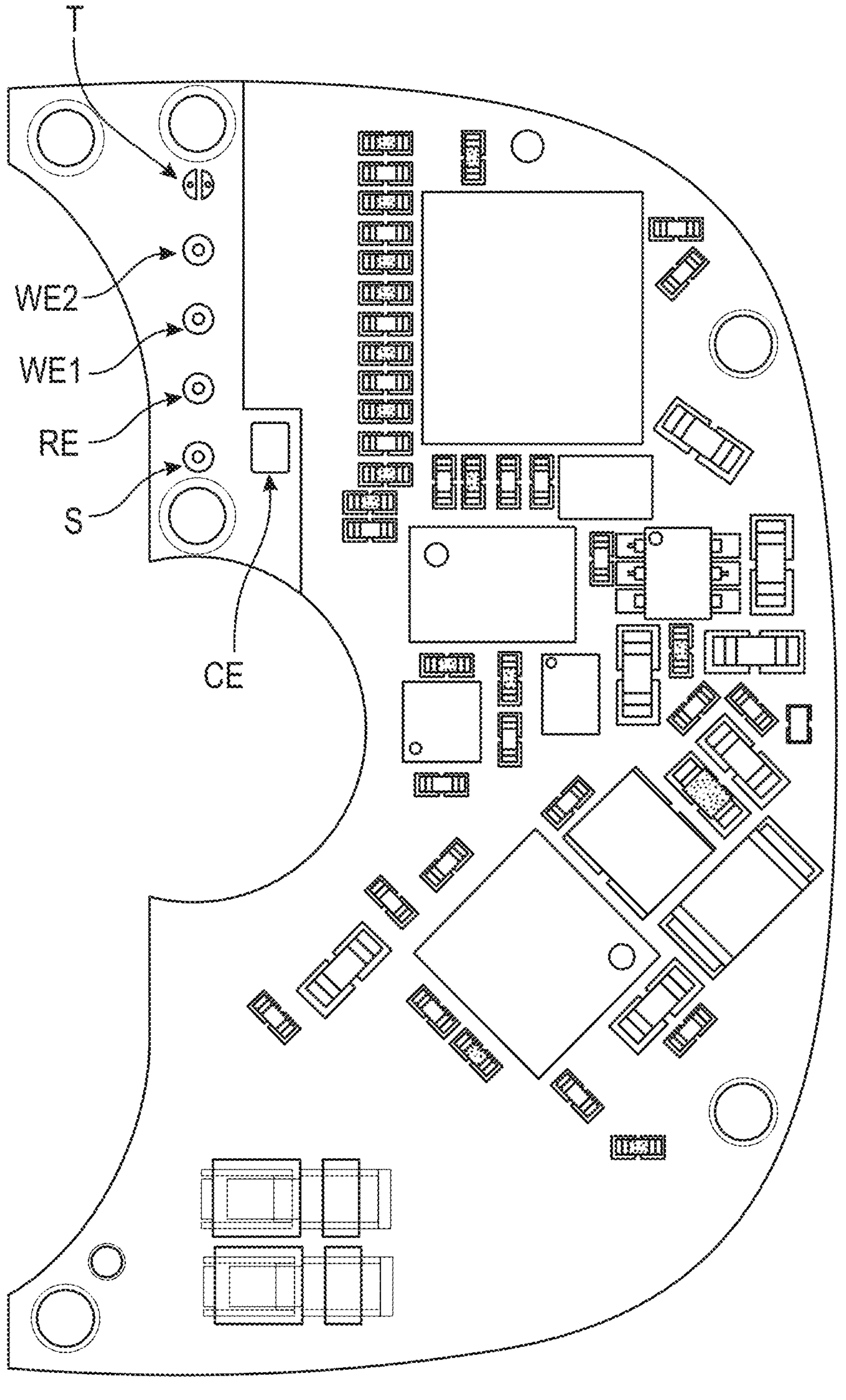
FIG. 8A illustrates the PCBA for connection to the sensor portion illustrated in FIG. 7.
Figure 8B:
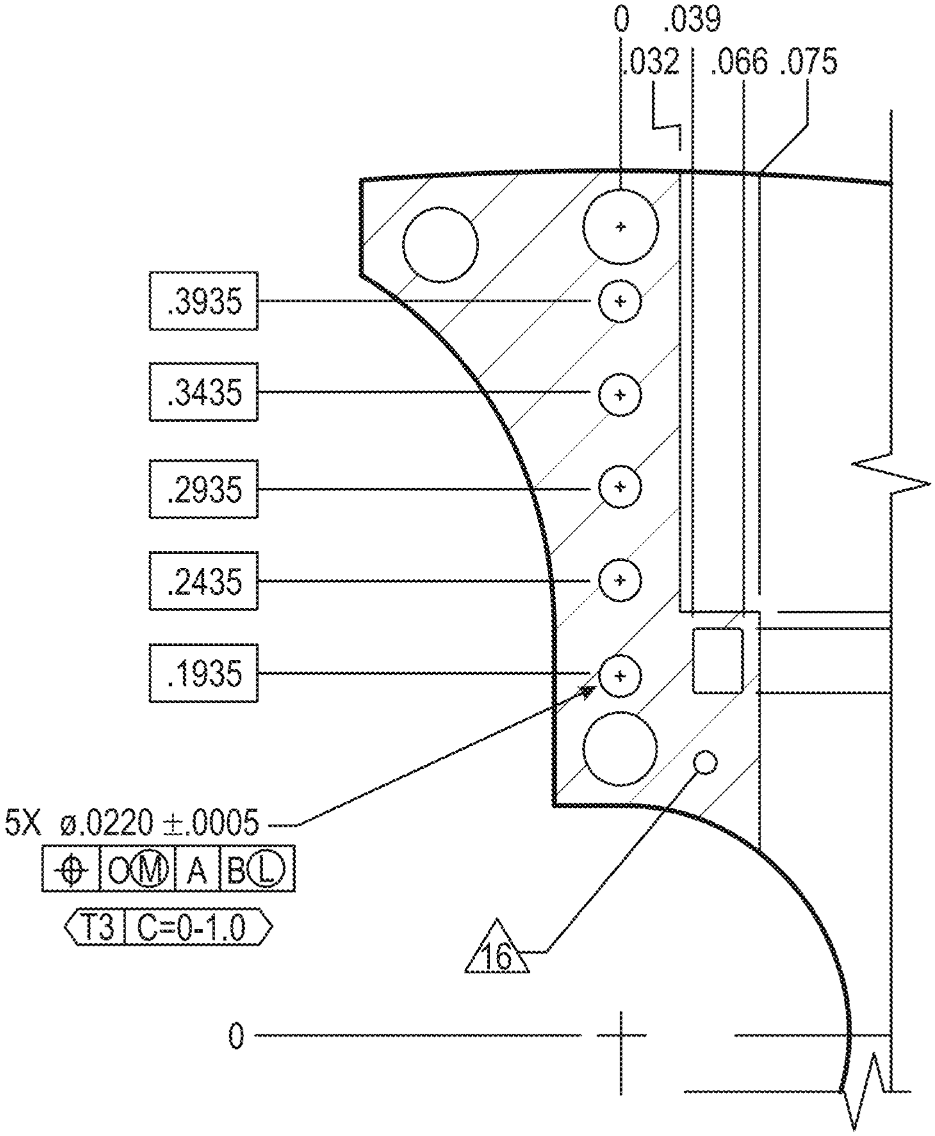
FIG. 8B illustrates sizing of the sensor connection pads on the PCBA according to one or more examples.

FIG. 7 illustrates an example sensing portion comprising a plurality of working electrodes (WE1, WE2); a counter electrode (CE), and a reference electrode (RE). Contacts 105 on the sensor portion 102 comprise first test contact T and second test contact S. The circuit 128 comprises a first resistor RTS attached to (e.g., directly on) the sensing portion 102 and connecting the first test contact T to the second test contact S. FIGS. 8A and 8B illustrate the sensor connection contacts on the PCBA (wherein FIG. 8B illustrates example dimensions of the sensor connection pads).

Figure 9A:
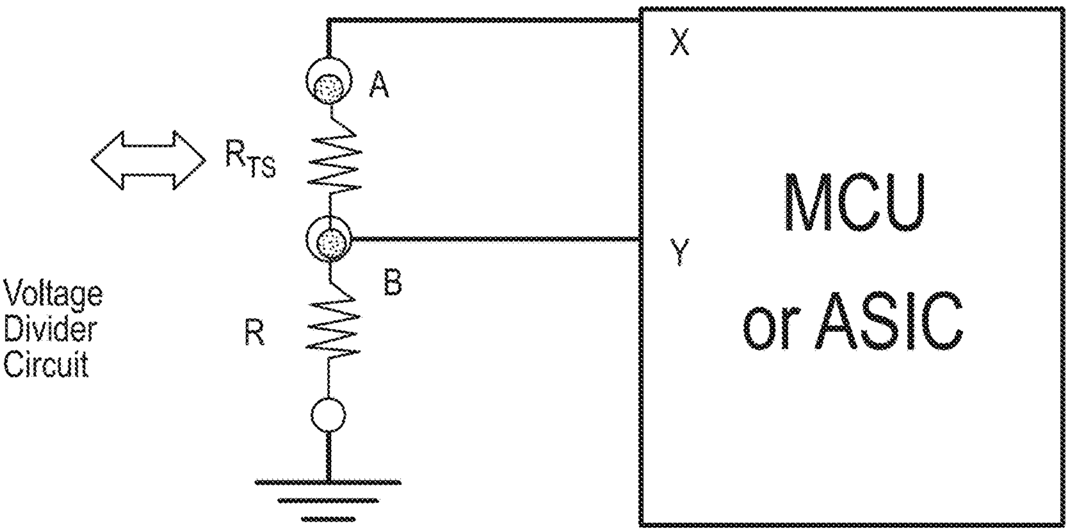
FIG. 9A illustrates a circuit including a voltage divider for detecting the electrical connection, according to a first configuration.
Figure 9B:
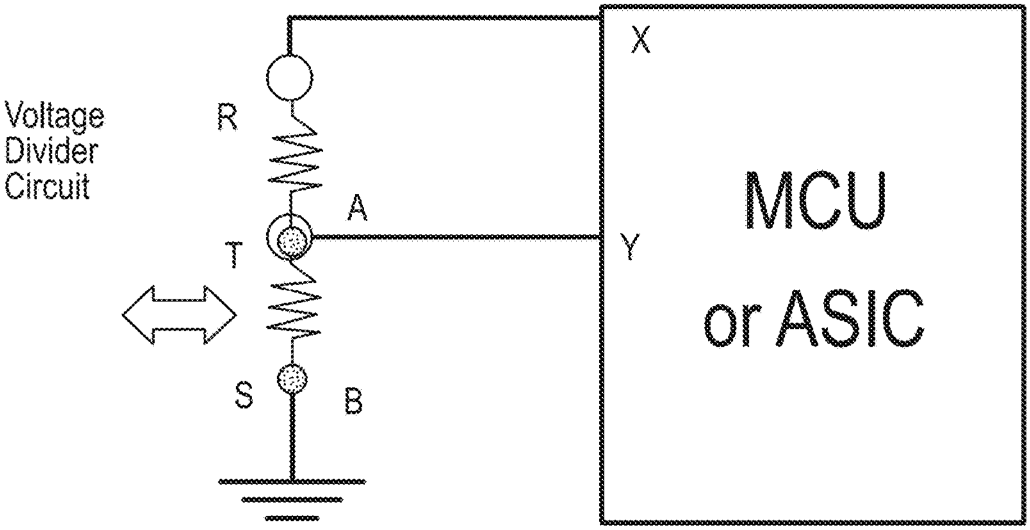
FIG. 9B illustrates a circuit including a voltage divider for detecting the electrical connection, according to a second configuration.
Figure 9C:
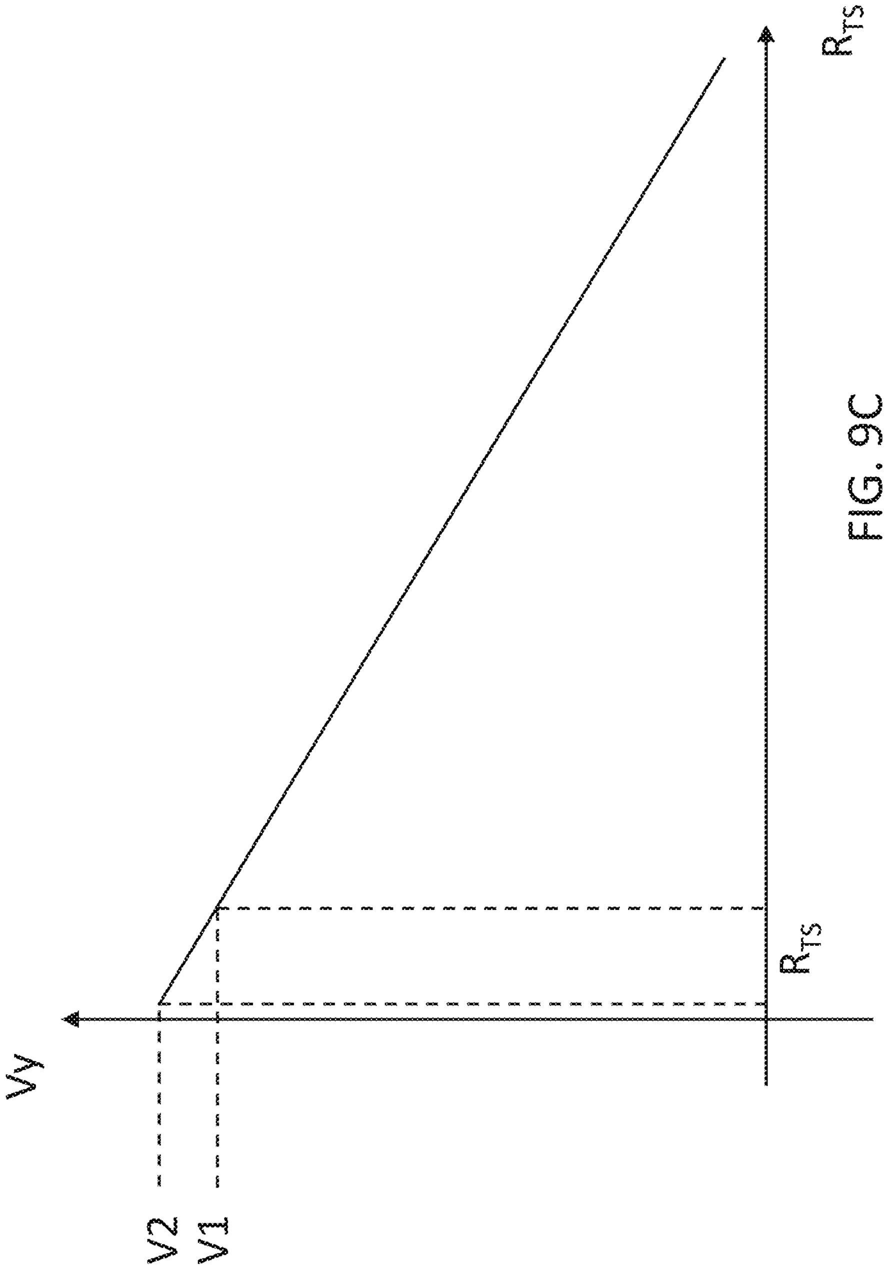
FIG. 9C illustrates measurement of Vy in a voltage divider circuit of FIG. 9A to determine operable electrical connection.

FIGS. 9A-9B illustrate the circuit 128 includes a voltage divider circuit comprising a second resistor (R on the PCBA) connected in series with the first resistor RTS, wherein the circuit 128 measures a potential difference across the first resistor. More specifically, the circuit measures a test voltage at a node between the first resistor and the second resistor so as to measure the potential difference across the first resistor used to detect the electrical connection 110. In the examples illustrated in FIG. 9A or 9B, the ASIC or MCU applies a known voltage at x (Vx) and measures the Vy voltage at y, Vy=Vx/(R+RTS). FIG. 9C illustrates that if Vy is in a predetermined range V1-V2 corresponding to the known RTS, there is a operable electrical connection 110 for proper operation of the analyte sensor apparatus and the PCBA is matched to the correct sensor portion 102.

In one or more examples, the circuit 128 indicates a proper electrical connection when the test voltage or potential difference across the first resistor is above a predetermined threshold confirming that the electrical connection is sufficient for measuring the concentration level of the analyte.

In one or more examples, second resistor R has fixed value and resistor RTS (between node T and S) on the sensor portion is unique to a given type of sensor platform. In one example, RTS is 1 kOhm for a first type of sensor portion or sensor portion in product line A and RTS is 10 kOhm for a second type of sensor portion or sensor portion in a product line B. In this example, if the voltage divider measures RTS=1 kOhm then the sensor portion is identified by the circuit as the first type of sensor portion in product line A and if the voltage divider measures RTS=10 kOhm then the sensor portion is identified by the circuit as the second type of sensor portion in product line B. In this way, the voltage divider circuit can also be used to identify the sensor portion correctly matched to the PCBA. In one or more examples, the first resistor has a resistance in a range of 0.1 ohms to 100 megaohms.

In one or more examples, the first resistor RTS has a resistance tagging the sensor portion so that the test voltage can be used to identify at least one of:

(1) a product line or generation associated with sensor portion,
(2) a type of analyte sensor or type of analyte measured using the sensor portion (e.g., glucose sensor, ketone sensor, lactate sensor measuring the analyte comprising glucose, a ketone, or a lactate, respectively,
(3) a batch or lot comprising the sensor portion, or
(4) a calibration needed to measure the concentration level using the sensor portion.

In one or more examples, the resistance of the first resistor enables identification of a sensor portion within a product line, or identification of a characteristic associated with the sensor portion, e.g., a serial number, lot number, batch number, manufacturing location, manufacturing date of the sensor portion.

In one or more further examples, the measured resistance value is used as an input to calculate the analyte concentration of the analyte.

In yet further examples, the measured resistance value is inputted to an algorithm executed by one or more of the processors on the PCBA and used by the algorithm to calculate or determine the type of analyte and/or concentration level of the analyte.

In one or more further examples, at least one of the resistance, the test voltage, type of analyte sensor, batch or lot, or calibration are communicated to the transmitter for transmission off the analyte sensor apparatus to a computer system (e.g., server, cloud network, or database) for tracking, inventory management or updating, software updating, or other application. In one or more examples, identification of the sensor portion using the resistance enables proper calibration of the sensor portion (allowing application of the correct shift to the raw current signal or other signals used to measure the analyte, e.g., in an impedance or current measurement used to measure the concentration level.

Thus, the fifth example enables more robust device level testing and enables encoding of unique identifying information on the sensor portion.

Sixth Example: Split Pad and Voltage Divider

Figure 10:
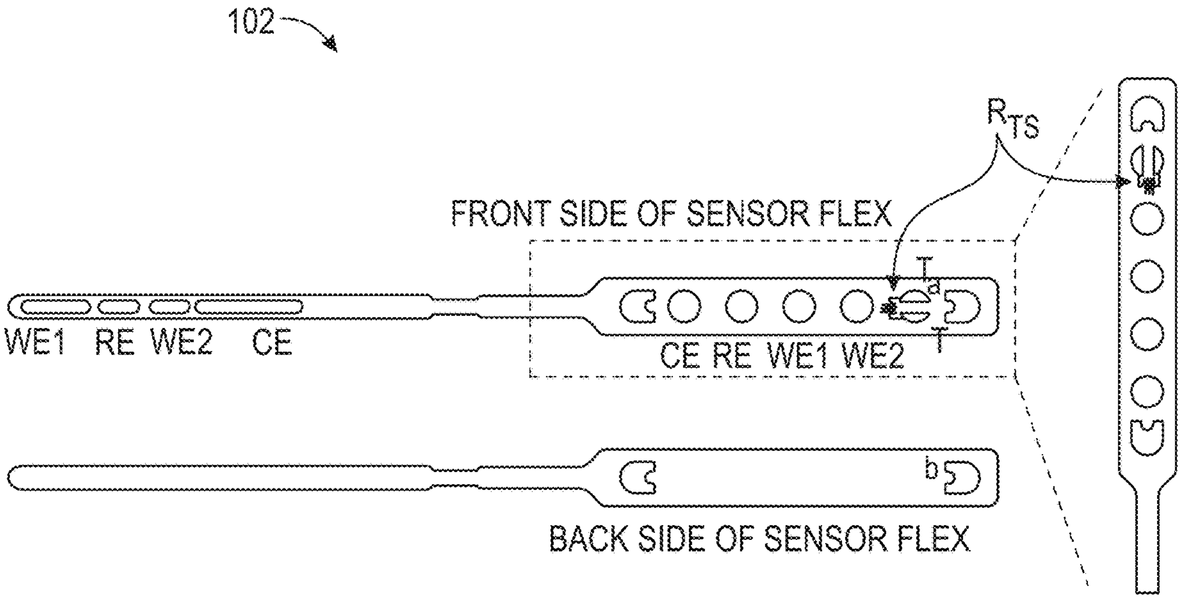
FIG. 10 illustrates a sensor portion according to another example used with a voltage divider.
Figure 11:
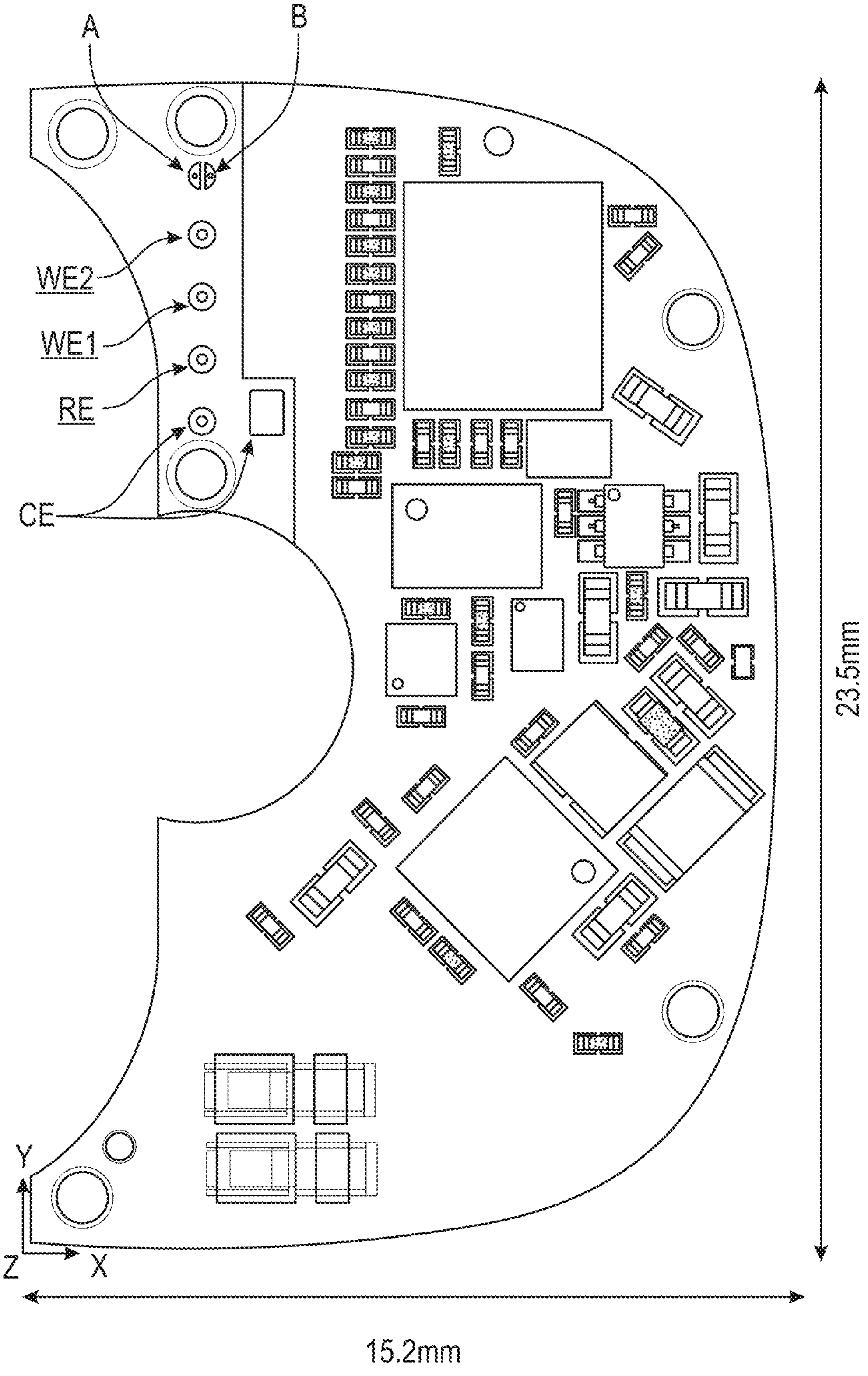
FIG. 11 illustrates the PCBA for connection to the sensor portion of the example of FIG. 10.
Figure 12:
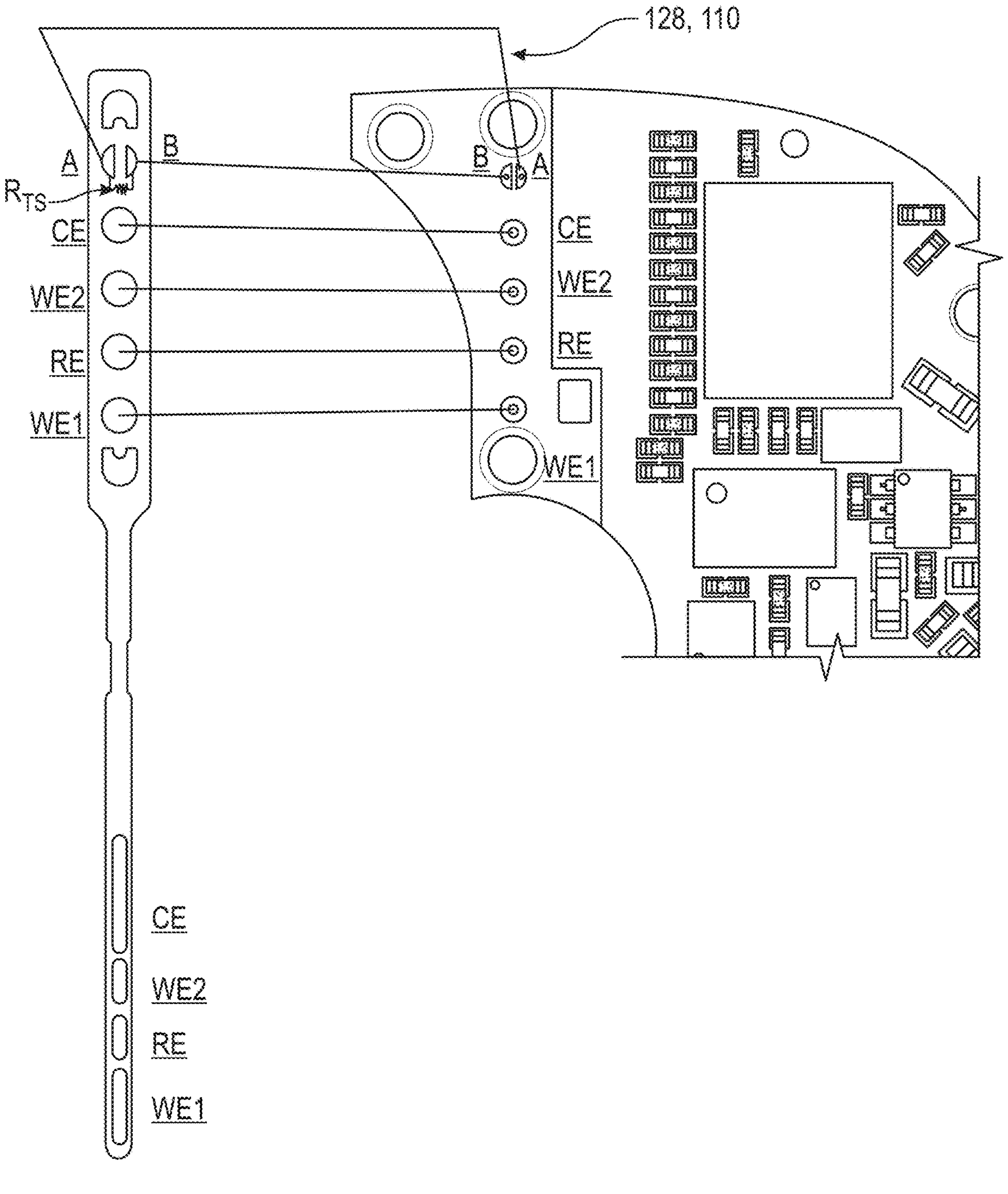
FIG. 12 illustrates the electrical connection between the sensor portion and the PCBA according to the example of FIG. 10.

FIG. 10 illustrates an example sensing portion comprising a plurality of working electrodes (WE1, WE2); a reference electrode (RE), and a counter electrode (CE). First conductive surfaces include first test pad or surface Ta and second test pad or surface Tb. The circuit 128 comprises a first resistor RTS attached to (e.g., directly on) the sensing portion 102 and connecting the first test pad Ta to the second test pad Tb. FIG. 11 illustrates the sensor connection pads on the PCBA and FIG. 12 illustrates the electrical connection between the sensor connection pads and the sensor portion.

The circuit 104 includes a voltage divider circuit comprising a second resistor (R on the PCBA) connected in series with the first resistor, wherein the circuit measures a potential difference across the first resistor. More specifically, the circuit measures a test voltage at a node between the first resistor and the second resistor so as to measure the potential difference across the first resistor used to detect the electrical connection 110.

In one or more examples, second resistor R has fixed value and resistor RTS between node A and B on the sensor portion (sensor flex) is unique to a given type of sensor platform. In one example, RTS is 1 kOhm for a first type of sensor portion or sensor portion in product line A and RTS is 10 kOhm for a second type of sensor portion or sensor portion in a product line B. In this example, if the voltage divider measures RTS=1 kOhm then the sensor portion is identified by the circuit as the first type of sensor portion in product line A and if the voltage divider measures RTS=10 kOhm then the sensor portion is identified by the circuit as the second type of sensor portion in product line B. In this way, the voltage divider circuit can also be used to identify the sensor portion.

Example Method of Making

Figure 13:
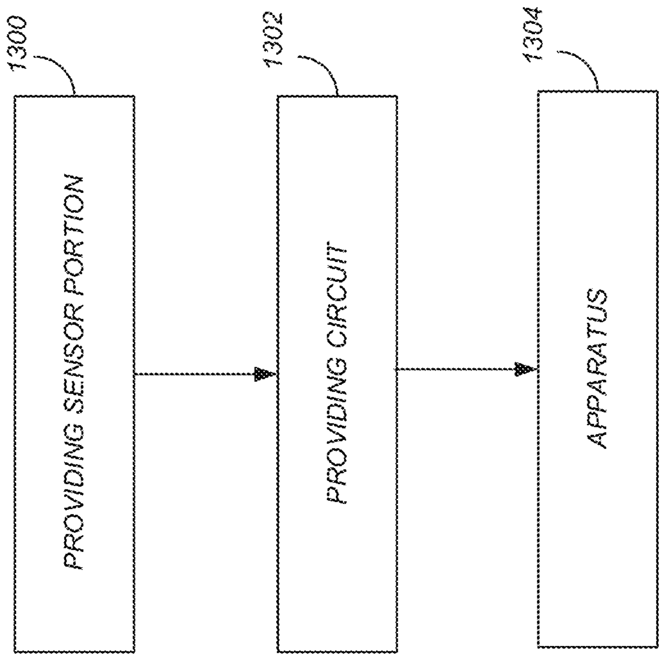
FIG. 13 is a flowchart illustrating a method of making an analyte sensor apparatus.

FIG. 13 is a flowchart illustrating a method of making an analyte sensor apparatus. The method comprises the following steps.

Block 1300 represents providing or making a sensing portion (e.g., sensor flex) including a working electrode; an analyte sensing layer on the working electrode, wherein the analyte sensing layer detectably alters an electrical current at the working electrode in a presence of an analyte; one or more electrodes establishing a reference potential of an environment comprising the analyte; and providing one or more contacts (contact pads) for connecting the sensor portion to a PCBA.

Block 1302 represents providing or making a circuit comprising the one or more contacts (contact pads comprising metal, metal regions, metallization), wherein the circuit detects an electrical connection between the one or more contacts and the PCBA and without requiring contact between the sensing portion and a fluid (e.g., a solution, water, the environment comprising the analyte).

In one or more examples, the step comprises providing the PCBA comprising one or more processors for receiving the electrical current and controlling a voltage applied to the one or more electrodes establishing the reference potential.

Block 1304 is the end result, an analyte sensor apparatus as illustrated herein.

Example Processing Environment

Figure 14:
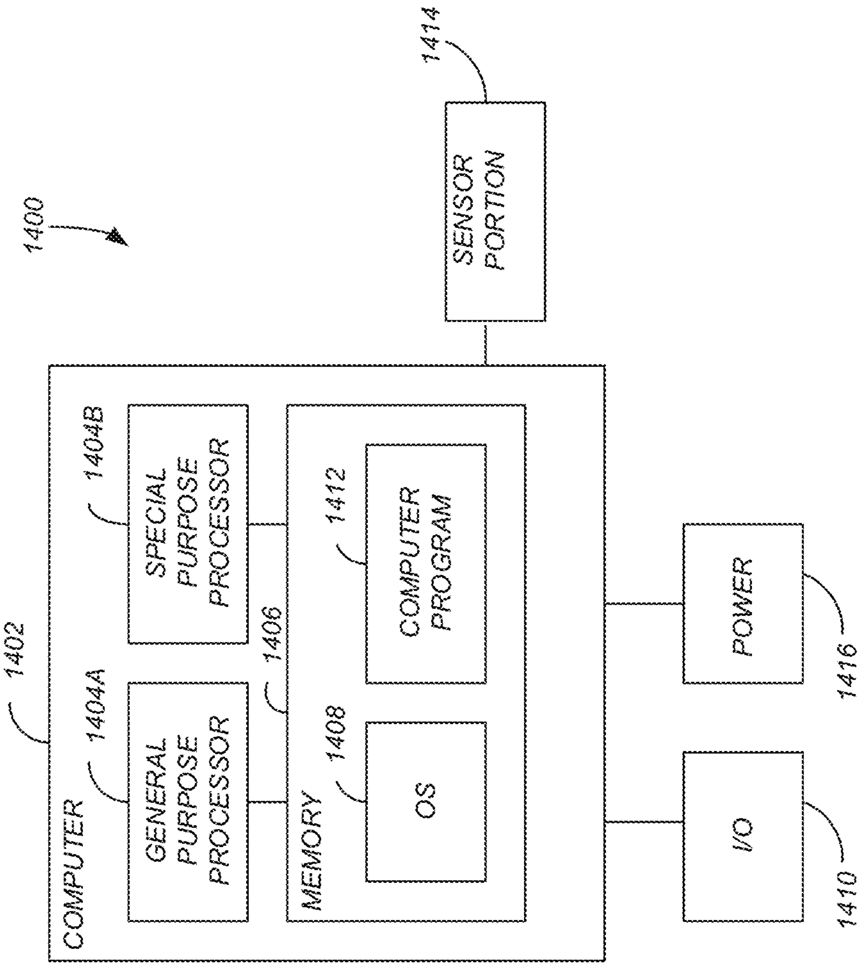
FIG. 14 is schematic of a hardware environment used to implement various processing functionalities described herein.

FIG. 14 illustrates an exemplary system 1400 comprising processors used to implement the processing functions and methods described herein.

The computer 1402 comprises a processor 1404 (general purpose processor 1404A and special purpose processor 1404B) and a memory, such as random access memory (RAM) 1406. Generally, the computer 1402 operates under control of an operating system 1408 stored in the memory 1406, and interfaces with the user/other computers to accept inputs and commands (e.g., analog or digital signals) and to present results through an input/output (I/O) module 1410. The computer program application 1412 accesses and manipulates data stored in the memory 1406 of the computer 1402. The operating system 1408 and the computer program 1412 are comprised of instructions which, when read and executed by the computer 1402, cause the computer 1402 to perform the operations herein described. In one embodiment, instructions implementing the operating system 1408 and the computer program 1410 are tangibly embodied in the memory 1406, thereby making a computer program product or article of manufacture. As such, the terms "article of manufacture," "program storage device" and "computer program product" as used herein are intended to encompass a computer program accessible from any computer readable device or media.

In one embodiment, computer 1402 comprises one or more field programmable gate arrays (FPGAs), application specific integrated circuits (ASICs), or microcontroller units (MCU).

The computer system 1400 is connected to the sensor portion 1414 via circuits described herein so as to receive electrical current Isig used to determine concentration of analyte, in response to application of the voltages to reference voltage (e.g., Vset) to counter electrode and/or a reference electrode. The computer system 1400 is also connected to test circuit 104 to control application and/or receive and analyze test signals from the test electrodes to detect the electrical connection 110.

FIG. 14 further illustrates a power source 1416 for providing power to the system 1400.

Those skilled in the art will recognize many modifications may be made to this configuration without departing from the scope of the present disclosure. For example, those skilled in the art will recognize that any combination of the above components, or any number of different components, peripherals, and other devices, may be used.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The descriptions and specific examples, while indicating some embodiments of the present invention are given by way of illustration and not limitation. Many changes and modifications within the scope of the present invention may be made without departing from the spirit thereof, and the invention includes all such modifications.

Example Method of Testing

Figure 15:
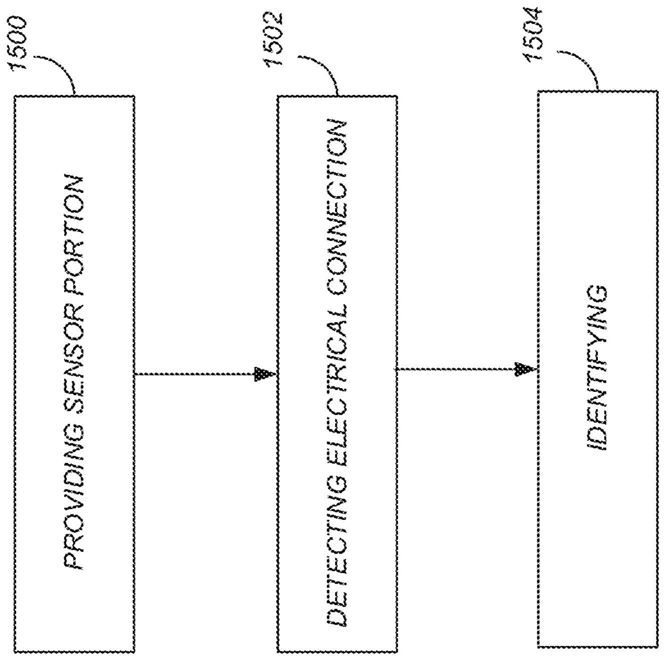
FIG. 15 is a flowchart illustrating a method of testing an analyte sensor apparatus.

FIG. 15 is a flowchart illustrating a method of testing an analyte sensor apparatus. The method comprises the following step.

Block 1500 represents providing a sensing portion including a working electrode; an analyte sensing layer on the working electrode, wherein the analyte sensing layer detectably alters an electrical current at the working electrode in a presence of an analyte; one or more electrodes establishing a reference potential of an environment comprising the analyte; and one or more test electrodes distinct from the working electrode and the one or more electrodes.

Block 1502 represents, using a circuit comprising the one or more contacts (e.g., contact pads), detecting or measuring an electrical connection between the one or more contacts and a Printed Circuit Board Assembly (PCBA) without contact between the sensing portion and the environment comprising the analyte. The PCBA comprises one or more processors for receiving the electrical current and controlling a voltage applied to the one or more electrodes establishing the reference potential.

Block 1504 represents outputting a test signal from the circuit in response to detecting the electrical connection and using the test signal to identify the sensor portion.

Device and Method Embodiments

An analyte sensor apparatus according to embodiments described herein is embodied in many ways including, but not limited to, the following.

1. An analyte sensor apparatus, comprising:
- a sensing portion 102 including:
- one or more electrodes 103 including a working electrode;
- an analyte sensing layer 410 on the working electrode, wherein the analyte sensing layer detectably alters an electrical current at the working electrode in a presence of an analyte; and
- a plurality of contacts 105 for electrically connecting the one or more electrodes to a printed circuit board assembly (PCBA), wherein:
- a circuit 128 comprising one or more of the contacts 105 detects an electrical connection 110 between the one or more of the contacts and the PCBA without requiring exposure of the sensor portion 102 to a fluid; and
- the PCBA comprises one or more processors 106 for receiving the electrical current and determining a concentration level of the analyte from the electrical current.

In one or more examples, the analyte sensor apparatus includes the circuit 128 comprising one or more of the contacts 105.

2. The analyte sensor apparatus of clause 1, further comprising:
- the contacts 105 including a first contact (T); and
- the PCBA further including a plurality of sensor connection contacts 118 for electrically connecting the PCBA to the sensing portion 102, the sensor connection contacts including a second contact (A) and a third contact (B); and wherein:
- the sensor portion in operable connection with the PCBA causes the first contact to physically contact both the second contact (A) and the third contact (B) so as to form the electrical connection 110 between the second contact (A) and the second contact (B), and
- the circuit 128 detects the electrical connection comprising a conduction path between the second contact and the third contact formed by the first contact physically contacting both the second contact (A) and the third contact (B).

3. The analyte sensor apparatus of clause 1, further comprising:

the contacts including a first contact (T); and the PCBA further including:

a plurality of sensor connection contacts for electrically connecting the PCBA to the sensing portion, the sensor connection contacts including a second contact (A), a third contact (B), and a fourth contact (C); and a first conductive track electrically connecting the second contact (A) to the fourth contact (C); and an elastomer connector comprising a second conductive track; and wherein:

the sensor portion in operable connection with the PCBA comprises:

the elastomer connector pressing the first contact (T) into physical and electrical contact with the fourth contact (C), the second conductive track electrically connecting the second contact (A) to the third contact (B), and the first conductive track and the second conductive track forming the electrical connection between the fourth contact (C), the third contact (B), the second contact (A), and the first contact (T); and wherein the circuit detects the electrical connection comprising a conduction path between the second contact (A) and the third contact (B).

4. The analyte sensor of clause 1, further comprising an elastomer connector 150 including a conductive track 650, wherein:

the PCBA comprises a plurality of sensor connection contacts 118 including a second contact (A) and a third contact (B);

the contacts 105 comprise a first contact 680 for electrically connecting one of the electrodes to the PCBA, wherein the first contact 680 is on a back side of the sensor portion 102 facing away from the PCBA; and the sensor portion in operable connection with the PCBA comprises the conductive track 650 forming the electrical connection between the first contact 680, the second contact (A), and the third contact (B).

5. The device of clause 4, wherein the one of the electrodes 103 comprises a counter electrode CE.

6. The analyte sensor apparatus of clause 1, further comprising an elastomeric connector 150 including a plurality of conductive tracks 650, wherein:

the PCBA comprises a plurality of sensor connection contacts 118 including a second contact (A) and a third contact (B);

the contacts 105 electrically connect the electrodes 103 to the PCBA and the contacts include a first contact (T); and the sensor portion 102 in operable connection with the PCBA comprises:

the contacts facing away from the PCBA;

each of the conductive tracks 650 electrically connecting one of the contacts 105 to one of the plurality of sensor connection contacts 118, and one of the conductive tracks 650 forming the electrical connection 110 between the first contact (T), the second contact (A), and the third contact (B).

7. The analyte sensor apparatus of any of the clauses 1-6, wherein:

the sensor PCBA comprises a plurality of sensor connection contacts 118 including a second contact (A) and a third contact (B); and the one or more processors 106 comprise:

an output (V) for applying a voltage V to one of the electrodes wherein the output is electrically connected to the second contact (A);

a check input (check) electrically connected to the third contact (B) and detecting the electrical connection between the second contact (A) and the third contact (B), and wherein the circuit measures a conduction path between the second contact (A) and the third contact (B) and one or more of the contacts on the sensor portion to detect the electrical connection 110.

8. The analyte sensor apparatus of any of the clauses 1-7, wherein the conduction path is characterized by a potential difference between the second contact (A) and the third contact (B) being less than 10% of a voltage applied by the circuit to the second contact (A) or the third contact (B) so as to measure the electrical connection.

9. The analyte sensor apparatus of claim 1, further comprising:

the contacts 105 comprising a first test contact T and a second test contact S;

the sensing portion 102 including a first resistor RTS electrically connecting the first test contact to the second test contact; and the circuit 128 including a second resistor on the PCBA and connected in series with the first resistor, wherein the circuit 128 measures a test voltage at a node between the first resistor and the second resistor so as to measure a potential difference across the first resistor used to detect the electrical connection 110.

10. The analyte sensor apparatus of clause 9, wherein the test voltage is above a predetermined threshold confirming that the electrical connection 110 is sufficient for measuring the concentration.

11. The analyte sensor apparatus of clause 9, wherein:

the first resistor has a resistance RTS tagging the sensor portion so that the test voltage and/or or the first resistance measured or determined from the test voltage can be used to identify at least one of:

a product line associated with the sensor portion 102, a type of analyte measured using the sensor portion, a batch or lot comprising the sensor portion, or a calibration needed to measure the concentration level using the sensor portion.

12. The analyte sensor apparatus of any of the clauses 9-11, wherein the first resistor has a resistance in a range of 0.1 Ohms-100 megaohms.

13. The analyte sensor apparatus of any of the clauses 9-12, further comprising using the test voltage to measure or determine the first resistance. In one or more examples, the analyte sensor apparatus includes a computer implemented system, comprising the one or more processors; one or more memories; and one or more programs or algorithms stored in the one or more memories, wherein the one or more programs or algorithms executed by the one or more processors determine the first resistance from the test voltage and use the first resistance to determine the type of analyte.

14. The analyte sensor apparatus of any of the clauses 9-12, further comprising a computer implemented system, comprising the one or more processors; one or more memories; and one or more programs or algorithms stored in the one or more memories, wherein the one or more programs or algorithms executed by the one or more processors:

determine the first resistance from the test voltage; and/or use the first resistance to calculate the concentration level of the analyte.

15. The analyte sensor of any of the clauses 9-14, further comprising a transmitter transmitting the first resistance and/or the test voltage tagging the sensor portion off the analyte sensor apparatus to a computer system tracking the sensor portion and/or providing updates using information (e.g., product line, batch/lot number, type of analyte, calibration) determined from the first resistance.

16. The analyte sensor apparatus of any of the clauses 1-15, wherein the contacts 105 comprise two adjacent portions or a split pad having a combined surface area no larger than a surface area of the working electrode.

17. The analyte sensor apparatus of any of the clauses 1-16, wherein:

the electrodes include one or more electrodes establishing a reference potential of the environment comprising the analyte, including:

a reference electrode establishing the reference potential, and a counter electrode maintaining a known voltage on the reference electrode, 18. The analyte sensor apparatus of any of the clauses 1-17, wherein:

the sensing portion comprises an electrical insulator, the electrodes including the working electrode and the conductive surfaces are disposed on a surface of the electrical insulator, the electrodes are spatially separated from each other along a first length of a distal end of the sensing portion, wherein the distal end is inserted into the environment during measurement of the analyte using the working electrode, and the one or more conductive surfaces are on a proximal end of the sensing portion attached to the PCBA during the measurement.

19. The analyte sensor apparatus of any of the clauses 1-18, wherein the electrodes have a diameter of 1000 micrometers or less of an area of 1000 by 1000 microns or less.

20. The analyte sensor apparatus of any of the clauses 1-19, wherein the circuit 128 detects the electrical connection in a non-hydrated environment. Conventional electronics cannot differentiate if the sensors is present (and non-hydrated) or not present.

21. The analyte sensor of any of the clauses 1-20, wherein the circuit 128 comprises a switch activating the circuit 128 during a testing mode of the analyte sensor apparatus and powering off the circuit afterward the electrical connection is detected so that the circuit is de-activated during normal operation of the analyte sensor apparatus measuring a concentration level of the analyte using the electrical current (e.g., using Electrochemical Impedance Spectroscopy), so as to not interfere with the normal operation of the analyte sensor apparatus.

22. The analyte sensor apparatus of any of the clauses 1-21, further comprising:

a battery connected to the processors for powering the processors;

an elastomer 150;

a housing housing the PCBA, the battery, and the elastomer, the housing comprising a top portion and a bottom portion, wherein closure of the housing attaching the top portion to the bottom portion clamps the first conductive surfaces between the elastomer and the PCBA so as to cause physical contact and the electrical connection between the first conductive surfaces and sensor connection pads on the PCBA;

an insertion needle connected to the sensing portion; and wherein:

the circuit outputs a test signal in response to detecting the electrical connection 110, and the one or more of the processors 106, 108 compute a concentration level of the analyte using the electrical current after:

receiving the test signal indicating the electrical connection of the PCBA to the sensing portion; and deployment of the sensing portion by the insertion needle into the in-vivo environment inside a body when the housing is attached to an exterior of the body.

23. The analyte sensor apparatus of clause 22, comprising a glucose sensor wherein:

the analyte sensing layer includes an enzyme having a composition that reacts with the analyte, comprising glucose, to form a byproduct, the byproduct detectably altering the electrical current at the working electrode, and the test signal indicates the electrical connection enabling the processors to compute the concentration level useful for determining an administration of insulin to the body of a diabetic patient.

24. A system comprising an insulin pump connected to the analyte sensor apparatus of clause 23, wherein the insulin pump delivers insulin to the diabetic patient depending on the concentration level measured after receiving the test signal indicating the electrical connection.

25. A method of testing an analyte sensor apparatus, comprising:

providing a sensing portion including:

a sensing portion including:

one or more electrodes including a working electrode;

an analyte sensing layer on the working electrode, wherein the analyte sensing layer detectably alters an electrical current at the working electrode in a presence of an analyte; and a plurality of first conductive surfaces for electrically connecting the one or more electrodes to a printed circuit board assembly (PCBA); and detecting an electrical connection using a circuit comprising one or more of the conductive surfaces, wherein:

the circuit detects the electrical connection between the one or more of the conductive surfaces and the PCBA when the sensing portion is disconnected from an in-vivo environment comprising the analyte; and the PCBA comprises one or more processors for receiving the electrical current and determining a concentration level of the analyte from the electrical current.

26. The method of clause 25, wherein the circuit outputs a test signal in response to detecting the electrical connection, the method further comprising using the test signal to identify the sensor portion.

27. The method of clause 25, further comprising using the circuit to detect the electrical connection in a non-hydrated environment.

28. The method of any of the clauses 25-27, further comprising powering off the circuit after detecting the electrical connection so that the circuit is de-activated during normal operation of the analyte sensor apparatus measuring a concentration level of the analyte using the electrical current.

29. The apparatus of any of the clauses 1-28 operated using the method of any of the clauses 19-22.

30. A method of making an analyte sensor apparatus, comprising:

providing a sensing portion including:

one or more electrodes including a working electrode;

an analyte sensing layer on the working electrode, wherein the analyte sensing layer detectably alters an electrical current at the working electrode in a presence of an analyte; and a plurality of first conductive surfaces for electrically connecting the one or more electrodes to a printed circuit board assembly (PCBA); and providing a circuit comprising one or more of the conductive surfaces, wherein:

the circuit detects an electrical connection between the one or more of the conductive surfaces and the PCBA when the sensing portion is disconnected from an in-vivo environment comprising the analyte; and the PCBA comprises one or more processors for receiving the electrical current and determining a concentration level of the analyte from the electrical current.

31. The method of clause 30, wherein the one or more electrodes establishing the reference potential comprise:

a reference electrode establishing the reference potential, and a counter electrode maintaining a known voltage on the reference electrode.

32. The apparatus of any of the clauses 1-31 manufactured using the method of any of the clauses 24-26.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The descriptions and specific examples, while indicating some embodiments of the present invention are given by way of illustration and not limitation. Many changes and modifications within the scope of the present invention may be made without departing from the spirit thereof, and the invention includes all such modifications.

What is claimed is:

1. An analyte sensor device comprising:

a housing;

a printed circuit board assembly (PCBA) within the housing and including a circuit and a first plurality of contacts; and a sensor comprising:

a proximal end within the housing, the proximal end including a second plurality of contacts electrically connected to the first plurality of contacts on the PCBA; and a distal end outside of the housing, the distal end including one or more electrodes configured to measure a concentration level of an analyte in a body of a user, wherein the circuit is operable to detect electrical connection between the first plurality of contacts and the second plurality of contacts within the housing while the distal end of the sensor is outside the body of the user or a fluid.

2. The analyte sensor device of claim 1, wherein the one or more electrodes include at least one working electrode, the at least one working electrode including an electrochemical sensing layer and electrically connected to a contact of the second plurality of contacts.

3. The analyte sensor device of claim 1, wherein:

the one or more electrodes include at least one working electrode, a reference electrode, and a counter electrode; and the second plurality of contacts on the sensor includes contacts electrically connected to the at least one working electrode, the reference electrode, and the counter electrode, and further includes a contact electrically isolated from the one or more electrodes and used for detecting the electrical connection between the first plurality of contacts and the second plurality of contacts.

4. The analyte sensor device of claim 1, wherein:

the second plurality of contacts on the sensor includes a first contact;

the first plurality of contacts on the PCBA includes a second contact and a third contact;

the first contact is configured to electrically connect the second contact to the third contact when the second plurality of contacts on the sensor is electrically connected to the first plurality of contacts on the PCBA; and the circuit is operable to detect the electrical connection between the first plurality of contacts and the second plurality of contacts based on detecting an electrical connection between the second contact and the third contact.

5. The analyte sensor device of claim 4, wherein the circuit is operable to apply a first voltage level to one contact of the second contact and the third contact, and measure a second voltage level at the other contact of the second contact and the third contact.

6. The analyte sensor device of claim 5, wherein the circuit detects the electrical connection between the second contact and the third contact in response to a potential difference between the second contact and the third contact being less than 10% of the first voltage level.

7. The analyte sensor device of claim 4, further comprising an elastomer configured to press the sensor toward the PCBA, such that the first contact physically contacts the second contact and the third contact.

8. The analyte sensor device of claim 1, further comprising an elastomer connector including a first conductive track, wherein:

the second plurality of contacts on the sensor includes a first contact;

the first plurality of contacts on the PCBA includes a second contact, a third contact, and a fourth contact electrically connected to the second contact via a second conductive track;

the elastomer connector is configured to press the sensor toward the PCBA to electrically connect the first contact to the fourth contact, and electrically connect the second contact to the third contact through the first conductive track; and the circuit is operable to detect the electrical connection between the first plurality of contacts and the second plurality of contacts based on detecting an electrical connection between the second contact and the third contact.

9. The analyte sensor device of claim 1, further comprising an elastomer connector including a conductive track, wherein:

the second plurality of contacts on the sensor includes a first contact on a side of the sensor opposing the PCBA and one or more contacts on a side of the sensor facing the PCBA;

the first plurality of contacts on the PCBA includes a second contact and a third contact;

the elastomer connector is configured to electrically connect the first contact, the second contact, and the third contact through the conductive track; and the circuit is operable to detect the electrical connection between the first plurality of contacts and the second plurality of contacts based on detecting an electrical connection between the second contact and the third contact.

10. The analyte sensor device of claim 1, further comprising an elastomer connector including a plurality of conductive tracks, wherein:

the second plurality of contacts is on a side of the sensor opposing the PCBA and includes a first contact;

the first plurality of contacts on the PCBA includes a second contact and a third contact; and each of the plurality of conductive tracks electrically connects one of the second plurality of contacts on the sensor to one of the first plurality of contacts on the PCBA, wherein a first conductive track of the plurality of conductive tracks electrically connects the first contact, the second contact, and the third contact.

11. The analyte sensor device of claim 1, wherein:

the second plurality of contacts includes a first test contact and a second test contact;

the sensor includes a first resistor electrically connecting the first test contact to the second test contact;

the first plurality of contacts includes a third test contact configured to electrically connect to the first test contact or the second test contact when the second plurality of contacts is electrically connected to the first plurality of contacts; and the circuit includes a second resistor electrically connected to the third test contact, wherein the circuit is operable to detect the electrical connection between the first plurality of contacts and the second plurality of contacts based on a voltage level at the third test contact.

12. The analyte sensor device of claim 11, wherein the first resistor and the second resistor form a voltage divider.

13. The analyte sensor device of claim 11, wherein the first plurality of contacts includes a fourth test contact configured to electrically connect to the first test contact or the second test contact when the second plurality of contacts is electrically connected to the first plurality of contacts.

14. The analyte sensor device of claim 11, wherein the circuit is further configured to determine, based on the voltage level at the third test contact, at least one of:

a product line associated with the sensor, a type of analyte measured using the sensor, a batch or lot comprising the sensor, or a calibration of the sensor for measuring the concentration level of the analyte.

15. The analyte sensor device of claim 11, wherein the circuit is configured to determine a resistance value of the first resistor based on the voltage level at the third test contact.

16. The analyte sensor device of claim 15, wherein the circuit includes a transmitter configured to transmit at least one of the voltage level at the third test contact or the determined resistance value of the first resistor to a computing system.

17. The analyte sensor device of claim 11, wherein the circuit includes a switch that is configurable to activate the circuit to detect the electrical connection between the first plurality of contacts and the second plurality of contacts in a test mode, and deactivate at least a portion of the circuit during an operation mode for measuring the concentration level of an analyte.

18. An analyte sensor device comprising:

a housing;

a printed circuit board assembly (PCBA) within the housing and including a circuit and a first plurality of contacts; and a sensor comprising:

a proximal end within the housing, the proximal end including a second plurality of contacts electrically connected to the first plurality of contacts on the PCBA; and a distal end outside of the housing, the distal end including one or more electrodes configured to measure a concentration level of an analyte in a body of a user, wherein the second plurality of contacts includes a first test contact that is electrically isolated from the one or more electrodes on the sensor and is configured to electrically connect to a second test contact of the first plurality of contacts on the PCBA, and wherein the circuit is electrically connected to the second test contact of the first plurality of contacts on the PCBA and is configured to detect electrical connection between the first plurality of contacts and the second plurality of contacts.

19. A method comprising:

activating a test circuit on a printed circuit board assembly (PCBA) positioned within a housing of an analyte sensor device, the PCBA including a first plurality of contacts, and the analyte sensor device including a sensor that includes:

a proximal end within the housing, the proximal end including a second plurality of contacts electrically connected to the first plurality of contacts on the PCBA; and a distal end outside of the housing, the distal end including one or more electrodes configured to measure a concentration level of an analyte in a body of a user, the second plurality of contacts including a first test contact that is electrically isolated from the one or more electrodes on the sensor and is configured to electrically connect to a second test contact of the first plurality of contacts on the PCBA;

applying, using the test circuit, a first voltage level to the second test contact;

measuring, using the test circuit, a second voltage level at a third test contact of the first plurality of contacts or a current at the second test contact or the third test contact; and determining, based on the measured second voltage level or the measured current, an electrical connection condition between the first plurality of contacts on the PCBA and the second plurality of contacts on the sensor.

20. The method of claim 19, further comprising, in response to determining that the electrical connection condition meets a criterion, deactivating at least a portion of the test circuit and initiating measurement of the concentration level of the analyte in the body of the user using the one or more electrodes on the sensor and a measurement circuit on the PCBA.

* * * * *